(12) United States Patent
Hull, III et al.

(10) Patent No.: US 9,255,096 B1
(45) Date of Patent: Feb. 9, 2016

(54) SUBSTITUTED 1,2,3,4-TETRAHYDROBENZO[C][2,7] NAPHTHYRIDINES AND DERIVATIVES THEREOF AS KINASE INHIBITORS

(71) Applicant: Allergan, Inc., Irvine, CA (US)

(72) Inventors: Clarence Eugene Hull, III, Mission Viejo, CA (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/508,982

(22) Filed: Oct. 7, 2014

(51) Int. Cl.
*C07D 471/00* (2006.01)
*C07D 491/00* (2006.01)
*C07D 471/04* (2006.01)

(52) U.S. Cl.
CPC .................................. *C07D 471/04* (2013.01)

(58) Field of Classification Search
CPC ........................... C07D 471/06; C07D 513/06
USPC ............................................ 546/79; 514/290
See application file for complete search history.

(56) References Cited

U.S. PATENT DOCUMENTS

| 7,601,736 B2 | 10/2009 | Kim et al. |
| 2006/0205772 A1 | 9/2006 | Coppola et al. |
| 2011/0212053 A1 | 9/2011 | Qian et al. |
| 2013/0338134 A1 | 12/2013 | Wu et al. |

OTHER PUBLICATIONS

Nobuo Jo, Carolina Mailhos,et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, Jun. 2006.
Justine R Smith, et al., Expression of vascular endothelial growth factor and its receptors in rosacea, Br J Ophthalmol 2007;91:226-229. doi: 10.1136/bjo.2006.101121.
S. W. Cowan-Jacob, et al., Structural biology of protein tyrosine kinases, Cell. Mol. Life Sci. 63 (2006) 2608-2625.
Regina Heidenreich, et al., Angiogenesis: The New Potential Target for the Therapy of Psoriasis?Drug News Perspect 21(2), Mar. 2008.
Aimee V. Chappelow et al., Neovascular Age-Related Macular Degeneration, Potential Therapies, Drugs 2008; 68 (8): 1029-1036.
Mark Rami Barakat, et al., VEGF inhibitors for the treatment of neovascular age-related macular degeneration, Expert Opin. Investig. Drugs (2009) 18(5).
Xinyuan Zhang, et al., Vascular endothelial growth factor-A: A multifunctional molecular player in diabetic retinopathy, The International Journal of Biochemistry & Cell Biology 41 (2009) 2368-2371.
Zhang Ni, et al., Emerging Pharmacologic Therapies for Wet Age-Related Macular Degeneration, Ophthalmologica 2009;223:401-410.
Jayne M. Stommel et al., Coactivation of Receptor Tyrosine Kinases Affects the Response of Tumor Cells to Targeted Therapies, www.sciencemag.org, Science vol. 318 Oct. 12, 2007.
Arora, A., et al., Role of Tyrosine Kinase Inhibitors in Cancer Therapy, J. Pharma. & Exper. Thera. 2005, 315: 971-979.
Bergers, G., et al., Benefits of targeting both pericytes and endothelial cells in the tumor vasculature with kinase inhibitors, J. Clin. Invest. 2003, 111: 1287-1295.
Cross, L.C., et al., Rules for the Nomenclature of Organic Chemistry, Pure & Applied Chem. 1976, 45: 11-30.
Stahl, Heinrich, et al., Handbook of Pharmaceutical Salts: Properties, Selection, and Use, 2002, 329-345.

*Primary Examiner* — Rita Desai
(74) *Attorney, Agent, or Firm* — Jonathan Bass

(57) ABSTRACT

The present invention relates to organic molecules capable of modulating tyrosine kinase signal transduction in order to regulate, modulate and/or inhibit abnormal cell proliferation.

10 Claims, No Drawings

SUBSTITUTED 1,2,3,4-TETRAHYDROBENZO[C][2,7] NAPHTHYRIDINES AND DERIVATIVES THEREOF AS KINASE INHIBITORS

FIELD OF THE INVENTION

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

DESCRIPTION OF THE RELATED ART

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2996, 63, 2608-2625

There are a number of examples where RTK kinases, have been found to be involved in cellular signaling pathways leading to pathological conditions, including exudative age-related macular degeneration (Ni et al. Opthalmologica 2009 223 401-410; Chappelow et al. Drugs 2008 68 1029-1036), diabetic retinopathy (Zhang et al., Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105), rosacea (Smith, J. R., V. B. Lanier, et al. Br J Ophthalmol 2007, 91(2): 226-229) and hyper immune response. In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFRβ may provide a greater therapeutic effect by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (DePinho et al., Science 2007 318 287-290; Bergers et al. J. Clin Invest. 2003 111 1287-1295).

US Patent Application No. US2011/0212053A1 discloses compounds of Formula:

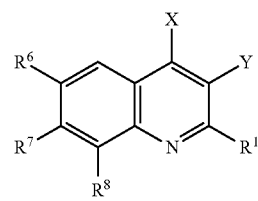

as inhibitors of PI3-kinase.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated PTKs transduction, including cell proliferative diseases such as cancer; vascular (blood vessel) proliferative disorders such as mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing and inflammation and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

In one aspect, the invention provides a compound represented by Formula I or a pharmaceutically acceptable salt thereof or stereoisomeric forms thereof, or the enantiomers, diastereoisomers, tautomers, zwitterions and pharmaceutically acceptable salts thereof:

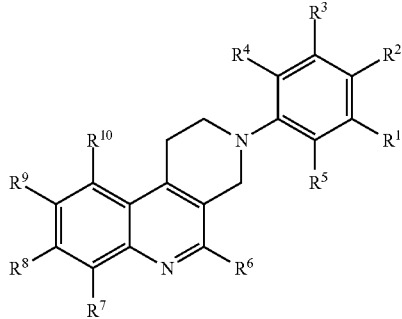

I wherein:
$R^1$ is $COOR^{11}$, $NH(CO)R^{12}$, $NH(CO)NR^{12}R^{13}$ or $CONR^{12}R^{13}$;

$R^2$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^3$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^4$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^5$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^6$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^7$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^8$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^9$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)$ $(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{10}$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{11}$ is hydrogen or substituted or unsubstituted $C_{1-12}$ alkyl;

$R^{12}$ is hydrogen, substituted or unsubstituted aryl, substituted or unsubstituted heterocyclic ring or substituted or unsubstituted $C_{1-12}$ alkyl;

$R^{13}$ is hydrogen, substituted or unsubstituted aryl, substituted or unsubstituted heterocyclic ring or substituted or unsubstituted $C_{1-12}$ alkyl;

$R^{14}$ is hydrogen or substituted or unsubstituted $C_{1-12}$ alkyl;
$R^{15}$ is hydrogen or substituted or unsubstituted $C_{1-12}$ alkyl;
$R^{16}$ is hydrogen or substituted or unsubstituted $C_{1-12}$ alkyl;
$R^{17}$ is hydrogen or substituted or unsubstituted $C_{1-12}$ alkyl;
$R^{18}$ is hydrogen or substituted or unsubstituted $C_{1-12}$ alkyl;
$R^{19}$ is hydrogen or substituted or unsubstituted $C_{1-12}$ alkyl; and p is 0, 1, 2, 3 or 4.

In another aspect, the invention provides a compound represented by Formula I wherein:

$R^1$ is $COOR^{11}$;

$R^2$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^3$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^4$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^5$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^6$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^7$ is hydrogen, substituted or unsubstituted $C_{1-12}$ alkyl, halogen, $OR^{19}$, $NR^{14}R^{15}$, $C(O)NR^{14}R^{15}$, $(CR^{18}R^{17})_pNR^{14}R^{15}$, $(CR^{18}R^{17})_pC(O)OR^{18}$, $(CR^{18}R^{17})_pOR^{18}$, $NR^{14}C(O)(CR^{18}R^{17})_pNR^{14}R^{15}$, $NR^{14}C(O)(CR^{18}R^{17})_pC(O)OR^{18}$, $NR^{14}C(O)(CR^{18}R^{17})_pOR^{18}$, $C(O)(CR^{18}R^{17})_pNR^{14}R^{15}$, $C(O)(CR^{18}R^{17})_pC(O)OR^{18}$, $C(O)(CR^{18}R^{17})_pCOR^{18}$, $C(O)NR^{15}(CR^{18}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{18}R^{17})_pOR^{18}$;

$R^8$ is hydrogen, substituted or unsubstituted $C_{1-12}$ alkyl, halogen, $OR^{19}$, $NR^{14}R^{15}$, $C(O)NR^{14}R^{15}$, $(CR^{18}R^{17})_pNR^{14}R^{15}$, $(CR^{18}R^{17})_pC(O)OR^{18}$, $(CR^{18}R^{17})_pOR^{18}$, $NR^{14}C(O)(CR^{18}R^{17})_pNR^{14}R^{15}$, $NR^{14}C(O)(CR^{18}R^{17})_pC(O)OR^{18}$, $NR^{14}C(O)(CR^{18}R^{17})_pOR^{18}$, $C(O)(CR^{18}R^{17})_pNR^{14}R^{15}$, $C(O)(CR^{18}R^{17})_pC(O)OR^{18}$, $C(O)(CR^{18}R^{17})_pCOR^{18}$, $C(O)NR^{15}(CR^{18}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{18}R^{17})_pOR^{18}$;

$R^9$ is hydrogen, substituted or unsubstituted $C_{1-12}$ alkyl, halogen, $OR^{19}$, $NR^{14}R^{15}$, $C(O)NR^{14}R^{15}$, $(CR^{18}R^{17})_pNR^{14}R^{15}$, $(CR^{18}R^{17})_pC(O)OR^{18}$, $(CR^{18}R^{17})_pOR^{18}$, $NR^{14}C(O)(CR^{18}R^{17})_pNR^{14}R^{15}$, $NR^{14}C(O)(CR^{18}R^{17})_pC(O)OR^{18}$, $NR^{14}C(O)(CR^{18}R^{17})_pOR^{18}$, $C(O)(CR^{18}R^{17})_pNR^{14}R^{15}$, $C(O)(CR^{18}R^{17})_pC(O)OR^{18}$, $C(O)(CR^{18}R^{17})_pCOR^{18}$, $C(O)NR^{15}(CR^{18}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{18}R^{17})_pOR^{18}$;

$R^{10}$ is hydrogen, substituted or unsubstituted $C_{1-12}$ alkyl, halogen, $OR^{19}$, $NR^{14}R^{15}$, $C(O)NR^{14}R^{15}$, $(CR^{18}R^{17})_pNR^{14}R^{15}$, $(CR^{18}R^{17})_pC(O)OR^{18}$, $(CR^{18}R^{17})_pOR^{18}$, $NR^{14}C(O)(CR^{18}R^{17})_pNR^{14}R^{15}$, $NR^{14}C(O)(CR^{18}R^{17})_pC(O)OR^{18}$, $NR^{14}C(O)(CR^{18}R^{17})_pOR^{18}$, $C(O)(CR^{18}R^{17})_pNR^{14}R^{15}$, $C(O)(CR^{18}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{11}$ is hydrogen or substituted or unsubstituted $C_{1-12}$ alkyl;
$R^{14}$ is hydrogen or substituted or unsubstituted $C_{1-12}$ alkyl;
$R^{15}$ is hydrogen or substituted or unsubstituted $C_{1-12}$ alkyl;
$R^{16}$ is hydrogen or substituted or unsubstituted $C_{1-12}$ alkyl;
$R^{17}$ is hydrogen or substituted or unsubstituted $C_{1-12}$ alkyl;
$R^{18}$ is hydrogen or substituted or unsubstituted $C_{1-12}$ alkyl;
$R^{19}$ is hydrogen or substituted or unsubstituted $C_{1-12}$ alkyl; and p is 0, 1, 2, 3 or 4.

In another aspect, the invention provides a compound represented by Formula I wherein:

$R^1$ is $CONR^{12}R^{13}$;

$R^2$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^3$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^4$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^5$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^6$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^7$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^8$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^9$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{10}$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{12}$ is hydrogen, substituted or unsubstituted aryl, substituted or unsubstituted heterocyclic ring or substituted or unsubstituted $C_{1-12}$ alkyl;

$R^{13}$ is hydrogen, substituted or unsubstituted aryl, substituted or unsubstituted heterocyclic ring or substituted or unsubstituted $C_{1-12}$ alkyl;

$R^{14}$ is hydrogen or substituted or unsubstituted $C_{1-12}$ alkyl;

$R^{15}$ is hydrogen or substituted or unsubstituted $C_{1-12}$ alkyl;

$R^{16}$ is hydrogen or substituted or unsubstituted $C_{1-12}$ alkyl;

$R^{17}$ is hydrogen or substituted or unsubstituted $C_{1-12}$ alkyl;

$R^{18}$ is hydrogen or substituted or unsubstituted $C_{1-12}$ alkyl;

$R^{19}$ is hydrogen or substituted or unsubstituted $C_{1-12}$ alkyl; and $p$ is 0, 1, 2, 3 or 4.

In another aspect, the invention provides a compound represented by Formula I wherein:

$R^1$ is $COOR^{11}$;

$R^2$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^3$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^4$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$,

9

NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^5$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^6$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^7$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^8$ is hydrogen, substituted or unsubstituted C$_{1-12}$ alkyl, halogen, OR$^{19}$, NR$^{14}$R$^{15}$, C(O)NR$^{14}$R$^{15}$, (CR$^{18}$R$^{17}$)$_p$NR$^{14}$R$^{15}$, (CR$^{18}$R$^{17}$)$_p$C(O)OR$^{18}$, (CR$^{18}$R$^{17}$)$_p$OR$^{18}$, NR$^{14}$C(O)(CR$^{18}$R$^{17}$)$_p$NR$^{14}$R$^{15}$, NR$^{14}$C(O)(CR$^{18}$R$^{17}$)$_p$C(O)OR$^{18}$, NR$^{14}$C(O)(CR$^{18}$R$^{17}$)$_p$OR$^{18}$, C(O)(CR$^{18}$R$^{17}$)$_p$NR$^{14}$R$^{15}$, C(O)(CR$^{18}$R$^{17}$)$_p$C(O)OR$^{18}$, C(O)(CR$^{18}$R$^{17}$)$_p$COR$^{18}$, C(O)NR$^{15}$(CR$^{18}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{18}$R$^{17}$)$_p$OR$^{18}$;

R$^9$ is hydrogen, substituted or unsubstituted C$_{1-12}$ alkyl, halogen, OR$^{19}$, NR$^{14}$R$^{15}$, C(O)NR$^{14}$R$^{15}$, (CR$^{18}$R$^{17}$)$_p$NR$^{14}$R$^{15}$, (CR$^{18}$R$^{17}$)$_p$C(O)OR$^{18}$, (CR$^{18}$R$^{17}$)$_p$OR$^{18}$, NR$^{14}$C(O)(CR$^{18}$R$^{17}$)$_p$NR$^{14}$R$^{15}$, NR$^{14}$C(O)(CR$^{18}$R$^{17}$)$_p$C(O)OR$^{18}$, NR$^{14}$C(O)(CR$^{18}$R$^{17}$)$_p$OR$^{18}$, C(O)(CR$^{18}$R$^{17}$)$_p$NR$^{14}$R$^{15}$, C(O)(CR$^{18}$R$^{17}$)$_p$C(O)OR$^{18}$, C(O)(CR$^{18}$R$^{17}$)$_p$COR$^{18}$, C(O)NR$^{15}$(CR$^{18}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{18}$R$^{17}$)$_p$OR$^{18}$;

R$^{10}$ is hydrogen, substituted or unsubstituted C$_{1-12}$ alkyl, halogen, OR$^{19}$, NR$^{14}$R$^{15}$, C(O)NR$^{14}$R$^{15}$, (CR$^{18}$R$^{17}$)$_p$NR$^{14}$R$^{15}$, (CR$^{18}$R$^{17}$)$_p$C(O)OR$^{18}$, (CR$^{18}$R$^{17}$)$_p$OR$^{18}$, NR$^{14}$C(O)(CR$^{18}$R$^{17}$)$_p$NR$^{14}$R$^{15}$, NR$^{14}$C(O)(CR$^{18}$R$^{17}$)$_p$C(O)OR$^{18}$, NR$^{14}$C(O)(CR$^{18}$R$^{17}$)$_p$OR$^{18}$, C(O)(CR$^{18}$R$^{17}$)$_p$NR$^{14}$R$^{15}$, C(O)(CR$^{18}$R$^{17}$)$_p$C(O)OR$^{18}$, C(O)(CR$^{18}$R$^{17}$)$_p$COR$^{18}$, C(O)NR$^{15}$(CR$^{18}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{18}$R$^{17}$)$_p$OR$^{18}$;

R$^{11}$ is hydrogen;

10

R$^{14}$ is hydrogen or substituted or unsubstituted C$_{1-12}$ alkyl;
R$^{15}$ is hydrogen or substituted or unsubstituted C$_{1-12}$ alkyl;
R$^{16}$ is hydrogen or substituted or unsubstituted C$_{1-12}$ alkyl;
R$^{17}$ is hydrogen or substituted or unsubstituted C$_{1-12}$ alkyl;
R$^{18}$ is hydrogen or substituted or unsubstituted C$_{1-12}$ alkyl;
R$^{19}$ is hydrogen or substituted or unsubstituted C$_{1-12}$ alkyl; and
p is 0, 1, 2, 3 or 4.

In another aspect, the invention provides a compound represented by Formula I wherein:

R$^1$ is COOR$^{11}$;

R$^2$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^3$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^4$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^5$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^6$ is hydrogen, substituted or unsubstituted C$_{1-12}$ alkyl, halogen, OR$^{19}$, NR$^{14}$R$^{15}$, C(O)NR$^{14}$R$^{15}$, (CR$^{16}$R$^{17}$)$_p$NR$^{14}$R$^{15}$, (CR$^{16}$R$^{17}$)$_p$C(O)OR$^{18}$, (CR$^{16}$R$^{17}$)$_p$OR$^{18}$, NR$^{14}$C(O)(CR$^{16}$R$^{17}$)$_p$NR$^{14}$R$^{15}$, NR$^{14}$C(O)(CR$^{16}$R$^{17}$)$_p$C(O)OR$^{18}$, NR$^{14}$C(O)(CR$^{16}$R$^{17}$)$_p$OR$^{18}$, C(O)(CR$^{16}$R$^{17}$)$_p$NR$^{14}$R$^{15}$, C(O)(CR$^{16}$R$^{17}$)$_p$C(O)OR$^{18}$, C(O)(CR$^{16}$R$^{17}$)$_p$COR$^{18}$, C(O)NR$^{15}$(CR$^{16}$R$^{17}$)$_p$NR$^{14}$R$^{15}$, C(O)NR$^{14}$(CR$^{16}$R$^{17}$)$_p$C(O)OR$^{18}$, C(O)NR$^{14}$(CR$^{16}$R$^{17}$)$_p$COR$^{18}$, NR$^{14}$C(O)NR$^{15}$(CR$^{16}$R$^{17}$)$_p$NR$^{14}$R$^{15}$, NR$^{14}$C(O)NR$^{15}$(CR$^{16}$R$^{17}$)$_p$C(O)OR$^{18}$ or NR$^{14}$C(O)NR$^{15}$(CR$^{16}$R$^{17}$)$_p$OR$^{18}$;

R$^7$ is hydrogen, substituted or unsubstituted C$_{1-12}$ alkyl, halogen, OR$^{19}$, NR$^{14}$R$^{15}$, C(O)NR$^{14}$R$^{15}$, (CR$^{18}$R$^{17}$)$_p$NR$^{14}$R$^{15}$, (CR$^{18}$R$^{17}$)$_p$C(O)OR$^{18}$, (CR$^{18}$R$^{17}$)$_p$OR$^{18}$, NR$^{14}$C(O)(CR$^{18}$R$^{17}$)$_p$NR$^{14}$R$^{15}$, NR$^{14}$C(O)(CR$^{18}$R$^{17}$)$_p$C(O)OR$^{18}$, NR$^{14}$C(O)(CR$^{18}$R$^{17}$)$_p$OR$^{18}$, C(O)(CR$^{18}$R$^{17}$)$_p$NR$^{14}$R$^{15}$, C(O)(CR$^{18}$R$^{17}$)$_p$C(O)OR$^{18}$, C(O)(CR$^{18}$R$^{17}$)$_p$COR$^{18}$, C(O)

$NR^{15}(CR^{18}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{18}R^{17})_pOR^{18}$;

$R^8$ is hydrogen, substituted or unsubstituted $C_{1-12}$ alkyl, halogen, $OR^{19}$, $NR^{14}R^{15}$, $C(O)NR^{14}R^{15}$, $(CR^{18}R^{17})_pNR^{14}R^{15}$, $(CR^{18}R^{17})_pC(O)OR^{18}$, $(CR^{18}R^{17})_pOR^{18}$, $NR^{14}C(O)(CR^{18}R^{17})_pNR^{14}R^{15}$, $NR^{14}C(O)(CR^{18}R^{17})_pC(O)OR^{18}$, $NR^{14}C(O)(CR^{18}R^{17})_pOR^{18}$, $C(O)(CR^{18}R^{17})_pNR^{14}R^{15}$, $C(O)(CR^{18}R^{17})_pC(O)OR^{18}$, $C(O)(CR^{18}R^{17})_pCOR^{18}$, $C(O)NR^{15}(CR^{18}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{18}R^{17})_pOR^{18}$;

$R^9$ is hydrogen, substituted or unsubstituted $C_{1-12}$ alkyl, halogen, $OR^{19}$, $NR^{14}R^{15}$, $C(O)NR^{14}R^{15}$, $(CR^{18}R^{17})_pNR^{14}R^{15}$, $(CR^{18}R^{17})_pC(O)OR^{18}$, $(CR^{18}R^{17})_pOR^{18}$, $NR^{14}C(O)(CR^{18}R^{17})_pNR^{14}R^{15}$, $NR^{14}C(O)(CR^{18}R^{17})_pC(O)OR^{18}$, $NR^{14}C(O)(CR^{18}R^{17})_pOR^{18}$, $C(O)(CR^{18}R^{17})_pNR^{14}R^{15}$, $C(O)(CR^{18}R^{17})_pC(O)OR^{18}$, $C(O)(CR^{18}R^{17})_pCOR^{18}$, $C(O)NR^{15}(CR^{18}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{18}R^{17})_pOR^{18}$;

$R^{10}$ is hydrogen, substituted or unsubstituted $C_{1-12}$ alkyl, halogen, $OR^{19}$, $NR^{14}R^{15}$, $C(O)NR^{14}R^{15}$, $(CR^{18}R^{17})_pNR^{14}R^{15}$, $(CR^{18}R^{17})_pC(O)OR^{18}$, $(CR^{18}R^{17})_pOR^{18}$, $NR^{14}C(O)(CR^{18}R^{17})_pNR^{14}R^{15}$, $NR^{14}C(O)(CR^{18}R^{17})_pC(O)OR^{18}$, $NR^{14}C(O)(CR^{18}R^{17})_pOR^{18}$, $C(O)(CR^{18}R^{17})_pNR^{14}R^{15}$, $C(O)(CR^{18}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{11}$ is substituted or unsubstituted $C_{1-12}$ alkyl;

$R^{12}$ is hydrogen, substituted or unsubstituted aryl, substituted or unsubstituted heterocyclic ring or substituted or unsubstituted $C_{1-12}$ alkyl;

$R^{13}$ is hydrogen, substituted or unsubstituted aryl, substituted or unsubstituted heterocyclic ring or substituted or unsubstituted $C_{1-12}$ alkyl;

$R^{14}$ is hydrogen or substituted or unsubstituted $C_{1-12}$ alkyl;
$R^{15}$ is hydrogen or substituted or unsubstituted $C_{1-12}$ alkyl;
$R^{16}$ is hydrogen or substituted or unsubstituted $C_{1-12}$ alkyl;
$R^{17}$ is hydrogen or substituted or unsubstituted $C_{1-12}$ alkyl;
$R^{18}$ is hydrogen or substituted or unsubstituted $C_{1-12}$ alkyl;
$R^{19}$ is hydrogen or substituted or unsubstituted $C_{1-12}$ alkyl; and p is 0, 1, 2, 3 or 4.

In another aspect, the invention provides a compound represented by Formula I wherein:

$R^1$ is $CONR^{12}R^{13}$;

$R^2$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^3$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^4$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^5$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^6$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^7$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^8$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{16}$, $(CR^{16}R^{17})_pC(O)OR^{18}$, $(CR^{16}R^{17})_pOR^{18}$, $NR^{14}C(O)(CR^{16}R^{17})_pNR^{14}R^{16}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{16}$, $C(O)(CR^{16}R^{17})_pC(O)OR^{18}$, $C(O)(CR^{16}R^{17})_pCOR^{18}$, $C(O)NR^{16}(CR^{16}R^{17})_pNR^{14}R^{16}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{16}(CR^{16}R^{17})_pOR^{18}$;

$R^9$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_pNR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{10}$ is hydrogen, substituted or unsubstituted $C_{1-12}$ alkyl, halogen, $OR^{19}$, $NR^{14}R^{15}$, $C(O)NR^{14}R^{15}$, $(CR^{16}R^{17})_p$ $NR^{14}R^{15}$, $(CR^{16}R^{17})_pC(O)OR^{18}$, $(CR^{16}R^{17})_pOR^{18}$, $NR^{14}C(O)(CR^{16}R^{17})_pNR^{14}R^{15}$, $NR^{14}C(O)(CR^{16}R^{17})_pC(O)OR^{18}$, $NR^{14}C(O)(CR^{16}R^{17})_pOR^{18}$, $C(O)(CR^{16}R^{17})_pNR^{14}R^{15}$, $C(O)(CR^{16}R^{17})_pC(O)OR^{18}$, $C(O)(CR^{16}R^{17})_pCOR^{18}$, $C(O)NR^{15}(CR^{16}R^{17})_pNR^{14}R^{15}$, $C(O)NR^{14}(CR^{16}R^{17})_pC(O)OR^{18}$, $C(O)NR^{14}(CR^{16}R^{17})_pCOR^{18}$, $NR^{14}C(O)NR^{15}(CR^{16}R^{17})_pNR^{14}R^{15}$, $NR^{14}C(O)NR^{15}(CR^{16}R^{17})_pC(O)OR^{18}$ or $NR^{14}C(O)NR^{15}(CR^{16}R^{17})_pOR^{18}$;

$R^{12}$ is hydrogen;
$R^{13}$ is substituted or unsubstituted aryl;
$R^{14}$ is hydrogen or substituted or unsubstituted $C_{1-12}$ alkyl;
$R^{15}$ is hydrogen or substituted or unsubstituted $C_{1-12}$ alkyl;
$R^{16}$ is hydrogen or substituted or unsubstituted $C_{1-12}$ alkyl;
$R^{17}$ is hydrogen or substituted or unsubstituted $C_{1-12}$ alkyl;
$R^{18}$ is hydrogen or substituted or unsubstituted $C_{1-12}$ alkyl;
$R^{19}$ is hydrogen or substituted or unsubstituted $C_{1-12}$ alkyl; and
p is 0, 1, 2, 3 or 4.

In another aspect, the invention provides a compound represented by Formula I wherein:
$R^1$ is $CONR^{12}R^{13}$;
$R^2$ is hydrogen, substituted or unsubstituted $C_{1-12}$ alkyl, halogen or $OR^{19}$;
$R^3$ is hydrogen, substituted or unsubstituted $C_{1-12}$ alkyl, halogen or $OR^{19}$;
$R^4$ is hydrogen, substituted or unsubstituted $C_{1-12}$ alkyl, halogen or $OR^{19}$;
$R^5$ is hydrogen, substituted or unsubstituted $C_{1-12}$ alkyl, halogen or $OR^{19}$;
$R^6$ is hydrogen, substituted or unsubstituted $C_{1-12}$ alkyl, halogen or $OR^{19}$;
$R^7$ is hydrogen, substituted or unsubstituted $C_{1-12}$ alkyl, halogen or $OR^{19}$;
$R^8$ is hydrogen, substituted or unsubstituted $C_{1-12}$ alkyl, halogen or $OR^{19}$;
$R^9$ is hydrogen, substituted or unsubstituted $C_{1-12}$ alkyl, halogen or $OR^{19}$;
$R^{10}$ is hydrogen, substituted or unsubstituted $C_{1-12}$ alkyl, halogen or $OR^{19}$;
$R^{12}$ is hydrogen; and
$R^{13}$ is substituted or unsubstituted aryl; and
$R^{19}$ is substituted or unsubstituted $C_{1-12}$ alkyl.

In another aspect, the invention provides a compound represented by Formula I wherein:
$R^1$ is $CONR^{12}R^{13}$;
$R^2$ is hydrogen;
$R^3$ is hydrogen;
$R^4$ is hydrogen;
$R^5$ is hydrogen;
$R^6$ is hydrogen;
$R^7$ is hydrogen;
$R^8$ is hydrogen or $OR^{19}$;
$R^9$ is hydrogen or $OR^{19}$;
$R^{10}$ is hydrogen;
$R^{12}$ is hydrogen; and
$R^{13}$ is substituted or unsubstituted aryl; and
$R^{19}$ is substituted or unsubstituted $C_{1-12}$ alkyl.

The term "alkyl", as used herein, refers to saturated, monovalent or divalent hydrocarbon moieties having linear or branched moieties or combinations thereof and containing 1 to 12 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-8}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-8}$ alkyl groups, —$SC_{1-6}$ alkyl groups, —$C_{1-8}$ alkyl groups, —$C_{2-8}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon moiety having 2 to 6 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon moiety having 2 to 6 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, amide groups, ketone groups, alkylamino groups, amino groups, aryl groups, ester groups, ketone groups, carboxylic acid groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, $—OC_{1-6}$ alkyl groups, $—SC_{1-6}$ alkyl groups, $—C_{1-6}$ alkyl groups, $—C_{2-6}$ alkenyl groups, $—C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic. Aryl groups in $R^2$ can be meta or para substituted by X. Aryl groups in $R^2$ are meta substituted by X.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)$R^x$ wherein $R^x$ can be alkyl, aryl, cycloalkyl, cycloalkenyl, heterocycle as defined above.

The term "ester" as used herein, represents an organic compound having a carbonyl group linked to a carbon atom such as —C(O)O$R^x$ wherein $R^x$ can be alkyl, aryl, cycloalkyl, cycloalkenyl, heterocycle as defined above.

The term "amine" as used herein, represents a group of formula "—N$R^xR^y$", wherein $R^x$ and $R^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—SO$_2$—". The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)ON".

The term "nitro" as used herein, represents a group of formula "—NO$_2$".

The term "cyano" as used herein, represents a group of formula "—CN".

The term "amide" as used herein, represents a group of formula "—C(O)N$R^xR^y$," or "N$R^xR^y$C(O)—" wherein $R^x$ and $R^y$ can be the same or independently H, alkyl, aryl, cycloalkyl, cycloalkenyl, heterocycle as defined above.

The term "sulfonamide" as used herein, represents a group of formula "—S(O)$_2$N$R^xR^y$" wherein $R^x$ and $R^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Other defined terms are used throughout this specification:
"Ac" refers to acetyl
"Et" refers to ethyl
"iPr" refers to i-propyl
"Me" refers to methyl
"MeOH" refers to methanol
"PDGF" refers to platelet derived growth factor
"Ph" refers to phenyl
"PTKs" refers to protein tyrosine kinase
"RTKs" refers to receptor tyrosine kinase
"rt" refers to room temperature
"tBu" refers to t-butyl
"THF" refers to tetrahydrofuran
"VEGF" refers to vascular endothelial growth factor
"VEGFR" refers to vascular endothelial growth factor receptor Compounds of the invention are tabulated in Table 1.

TABLE 1

| Example Number | Structure | Compound Name |
|---|---|---|
| 1 | [structure: 1,4-dihydrobenzo[c]-2,7-naphthyridine linked at N to phenyl-CO$_2$Me] | Methyl 3-(1,4-dihydrobenzo[c]-2,7-naphthyridin-3(2H)-yl)benzoate |
| 2 | [structure: 1,4-dihydrobenzo[c]-2,7-naphthyridine linked at N to phenyl-CO$_2$H] | 3-(1,4-dihydrobenzo[c]-2,7-naphthyridin-3(2H)-yl)benzoic acid |

TABLE 1-continued

| Example Number | Structure | Compound Name |
|---|---|---|
| 3 | 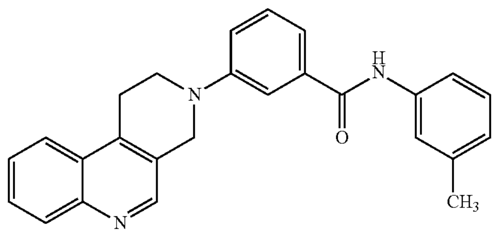 | 3-(1,4-dihydrobenzo[c]-2,7-naphthyridin-3(2H)-yl)-N-(3-methylphenyl)benzamide |
| 4 | 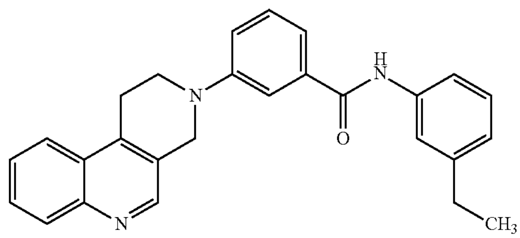 [SMILES: CCc1cccc(NC(=O)c2cccc(N3CCc4c(cnc5ccccc45)C3)c2)c1] | 3-(1,4-dihydrobenzo[c]-2,7-naphthyridin-3(2H)-yl)-N-(3-ethylphenyl)benzamide |
| 5 | 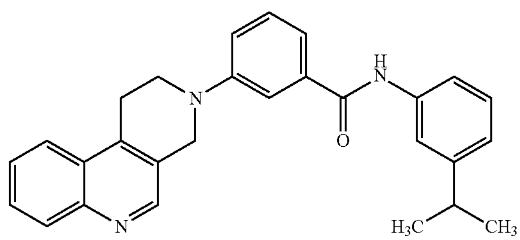 [SMILES: CC(C)c1cccc(NC(=O)c2cccc(N3CCc4c(cnc5ccccc45)C3)c2)c1] | 3-(1,4-dihydrobenzo[c]-2,7-naphthyridin-3(2H)-yl)-N-(3-isopropylphenyl)benzamide |
| 6 | 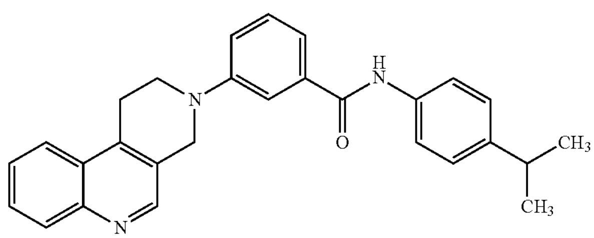 [SMILES: CC(C)c1ccc(NC(=O)c2cccc(N3CCc4c(cnc5ccccc45)C3)c2)cc1] | 3-(1,4-dihydrobenzo[c]-2,7-naphthyridin-3(2H)-yl)-N-(4-isopropylphenyl)benzamide |
| 7 | 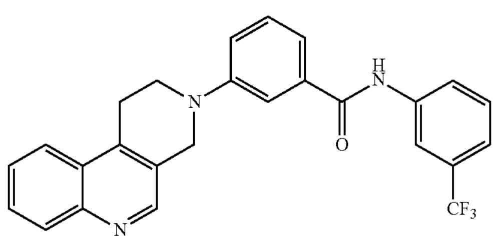 | 3-(1,4-dihydrobenzo[c]-2,7-naphthyridin-3(2H)-yl)-N-[3-(trifluoromethyl)phenyl]benzamide |
| 8 | 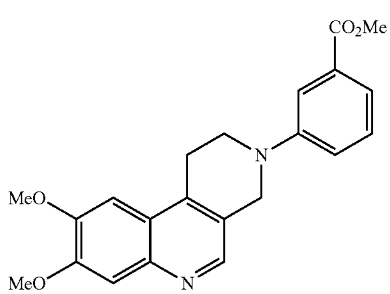 [SMILES: COC(=O)c1cccc(N2CCc3c(cnc4cc(OC)c(OC)cc34)C2)c1] | 8,9-dimethoxy-1,2,3,4-tetrahydrobenzo[c]-2,7-naphthyridine |

TABLE 1-continued

| Example Number | Structure | Compound Name |
|---|---|---|
| 9 | 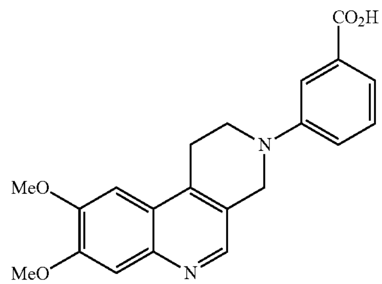 | 3-(8,9-dimethoxy-1,4-dihydrobenzo[c]-2,7-naphthyridin-3(2H)-yl)benzoic acid |
| 10 | 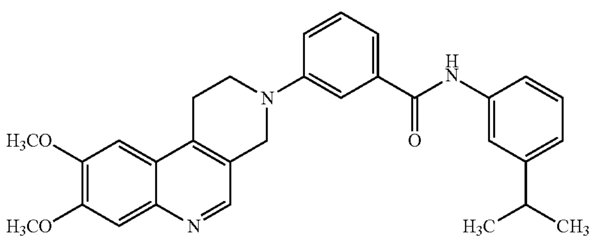 [SMILES: COc1cc2ncc3c(c2cc1OC)CCN(c1cccc(C(=O)Nc2cccc(C(C)C)c2)c1)C3] | 3-(8,9-dimethoxy-1,4-dihydrobenzo[c]-2,7-naphthyridin-3(2H)-yl)-N-(3-isopropylphenyl)benzamide |
| 11 | 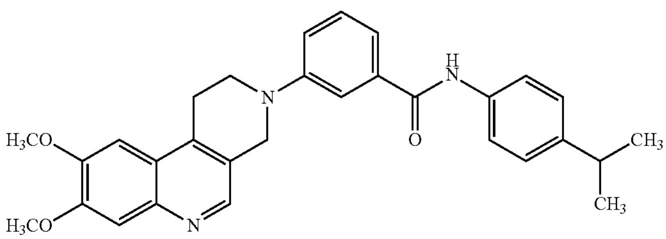 [SMILES: COc1cc2ncc3c(c2cc1OC)CCN(c1cccc(C(=O)Nc2ccc(C(C)C)cc2)c1)C3] | 3-(8,9-dimethoxy-1,4-dihydrobenzo[c]-2,7-naphthyridin-3(2H)-yl)-N-(4-isopropylphenyl)benzamide |
| 12 | 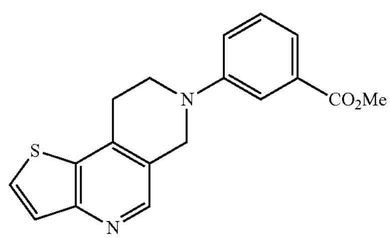 [SMILES: COC(=O)c1cccc(N2CCc3c(cnc4ccsc34)C2)c1] | methyl 3-(8,9-dihydrothieno[3,2-c]-2,7-naphthyridin-7(6H)-yl)benzoate |
| 13 | 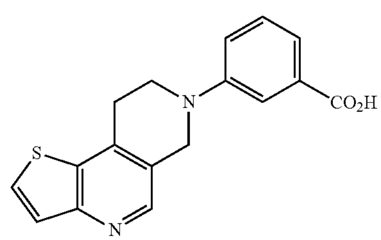 [SMILES: O=C(O)c1cccc(N2CCc3c(cnc4ccsc34)C2)c1] | 3-(8,9-dihydrothieno[3,2-c]-2,7-naphthyridin-7(6H)-yl)benzoic acid |
| 14 | 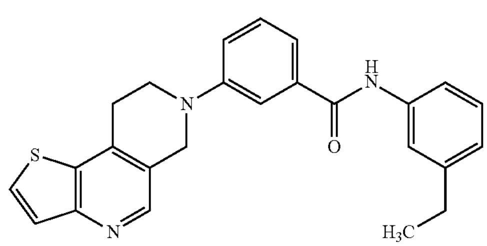 [SMILES: CCc1cccc(NC(=O)c2cccc(N3CCc4c(cnc5ccsc45)C3)c2)c1] | 3-(8,9-dihydrothieno[3,2-c]-2,7-naphthyridin-7(6H)-yl)-N-(3-ethylphenyl)benzamide |

Compounds of formula I are useful as protein kinase inhibitors. As such, compounds of formula I will be useful for treating diseases related to protein kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

The fibrotic disorder is selected from the group consisting of hepatic cirrhosis and atherosclerosis.

The mesangial cell proliferative disorder is selected from the group consisting of glomerulonephritis, diabetic nephropathy, malignant nephrosclerosis, thrombotic microangiopathy syndromes, transplant rejection and glomerulopathies.

The metabolic disease is selected from the group consisting of psoriasis, diabetes mellitus, wound healing, inflammation and neurodegenerative diseases.

The blood vessel proliferative disorder is selected from the group consisting of diabetic retinopathy, exudative age-related macular degeneration, retinopathy of prematurity, pterigium, rosacea, arthritis and restenosis.

Some compounds of Formula I and some of their intermediates may have at least one asymmetric center in their structure. This asymmetric center may be present in an R or S configuration, said R and S notation is used in correspondence with the rules described in Pure Applied Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta—Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum *acacia*, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or *acacia*, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:
Ingredient Amount (% w/v)
active ingredient about 0.001-5
preservative 0-0.10
vehicle 0-40
tonicity adjustor 0-10
buffer 0.01-10
pH adjustor q.s. pH 4.5-7.8
antioxidant as needed
surfactant as needed
purified water to make 100%

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 μl.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy.

The present invention concerns also processes for preparing the compounds of Formula I. The compounds of formula I according to the invention can be prepared analogously to conventional methods as understood by the person skilled in the art of synthetic organic chemistry. Synthetic Schemes set forth below, illustrate how the compounds according to the invention can be made.

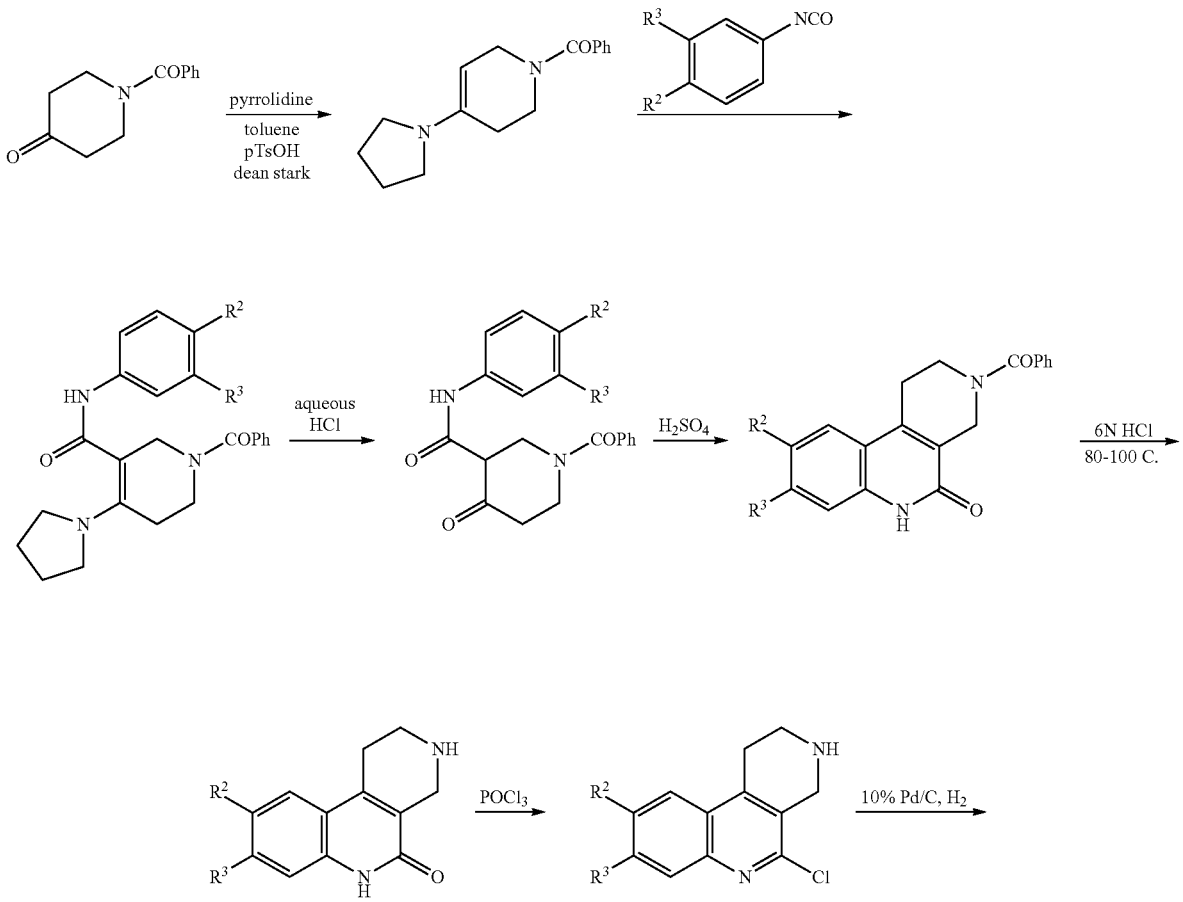

-continued
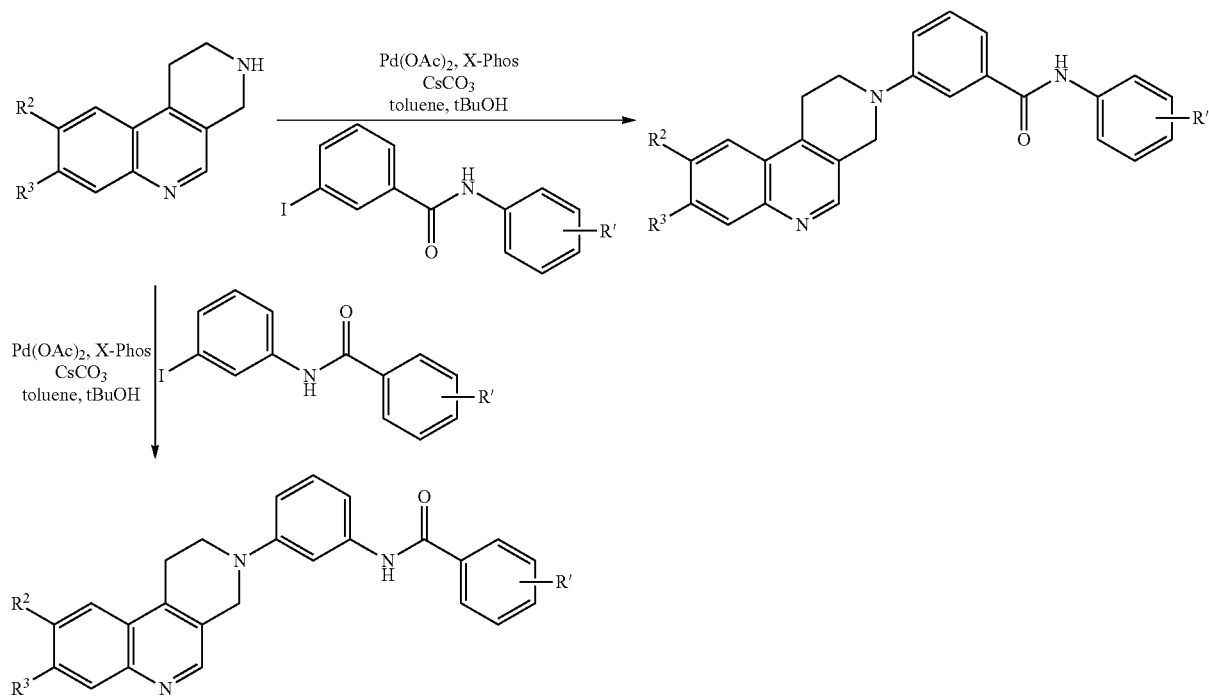
R' = simple alkyl, halogen, CF₃
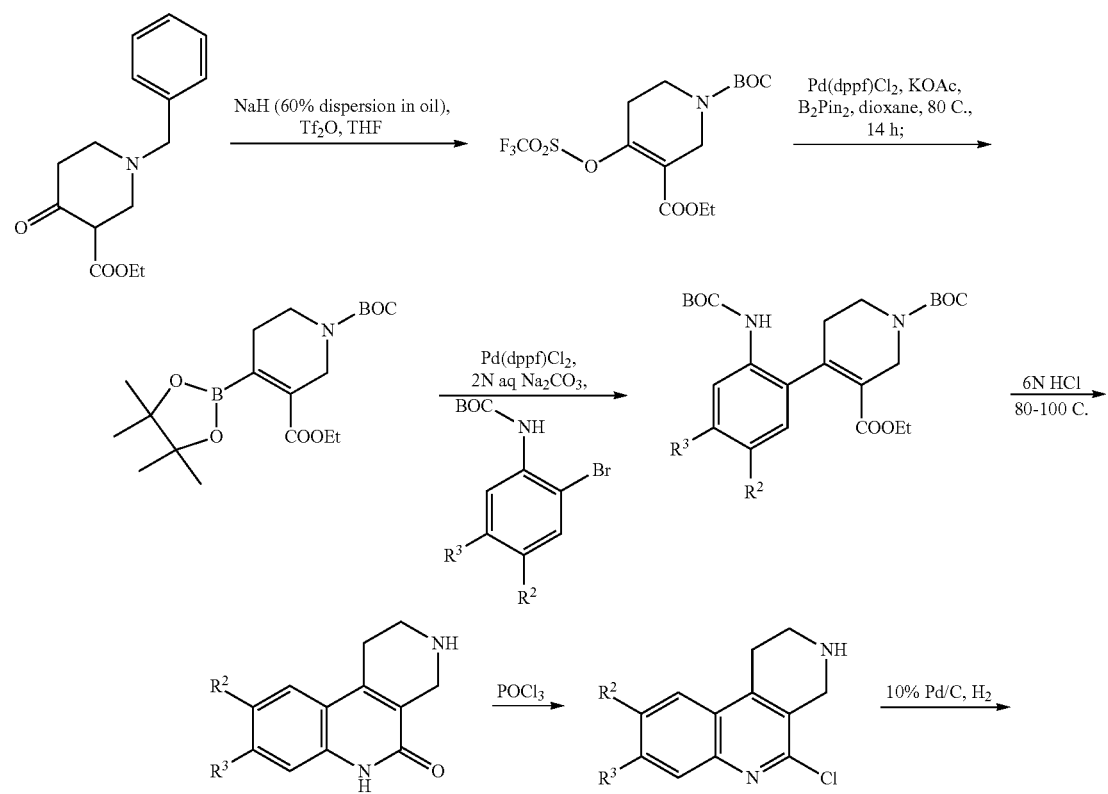

-continued
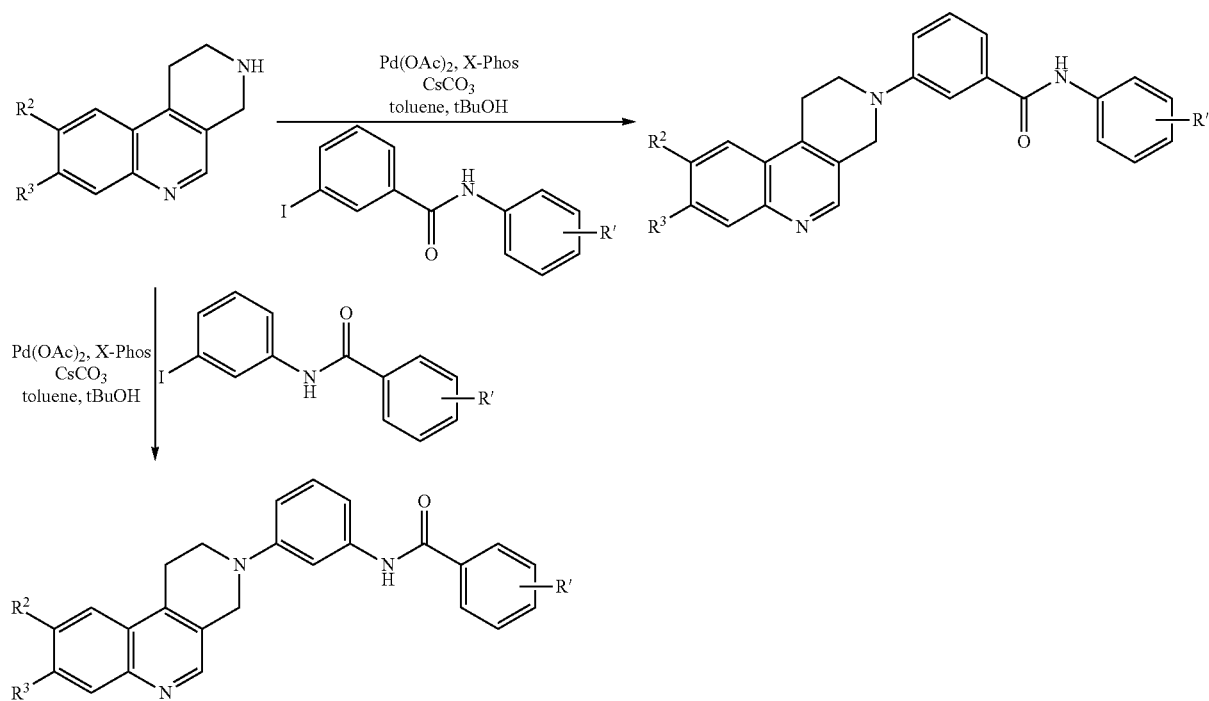
R' = simple alkyl, halogen, CF₃
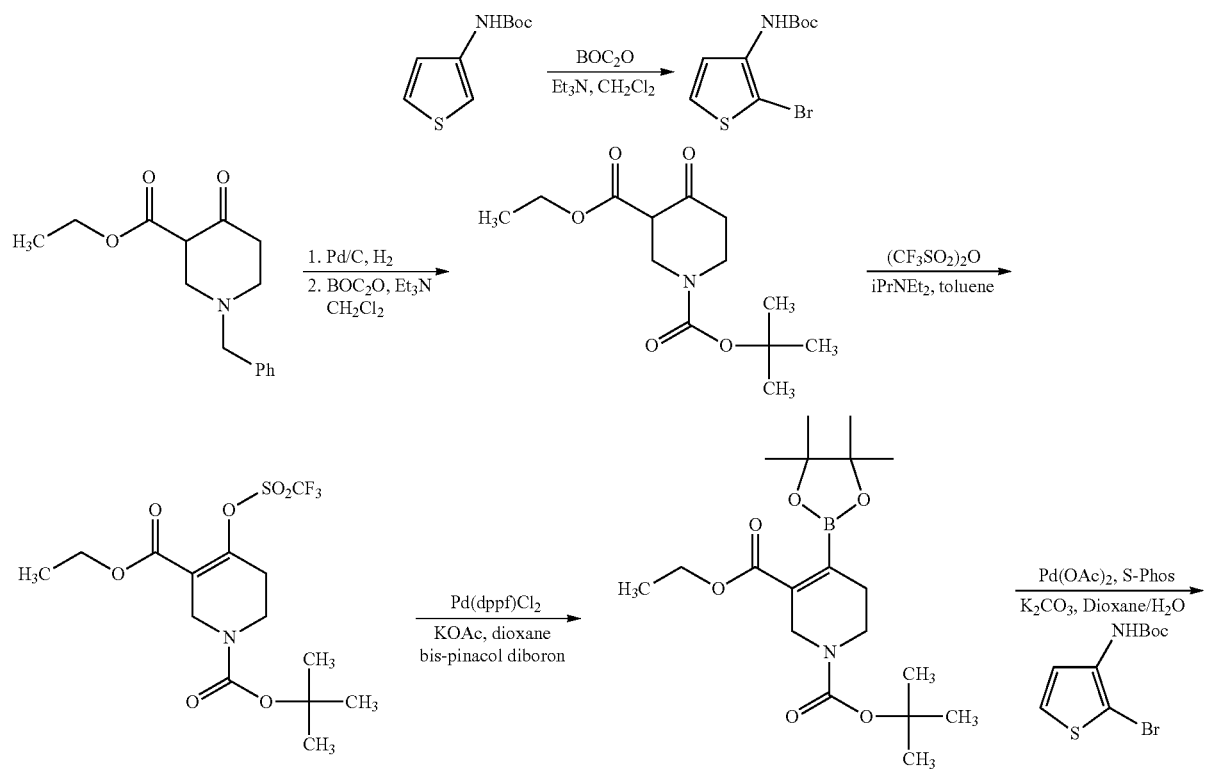

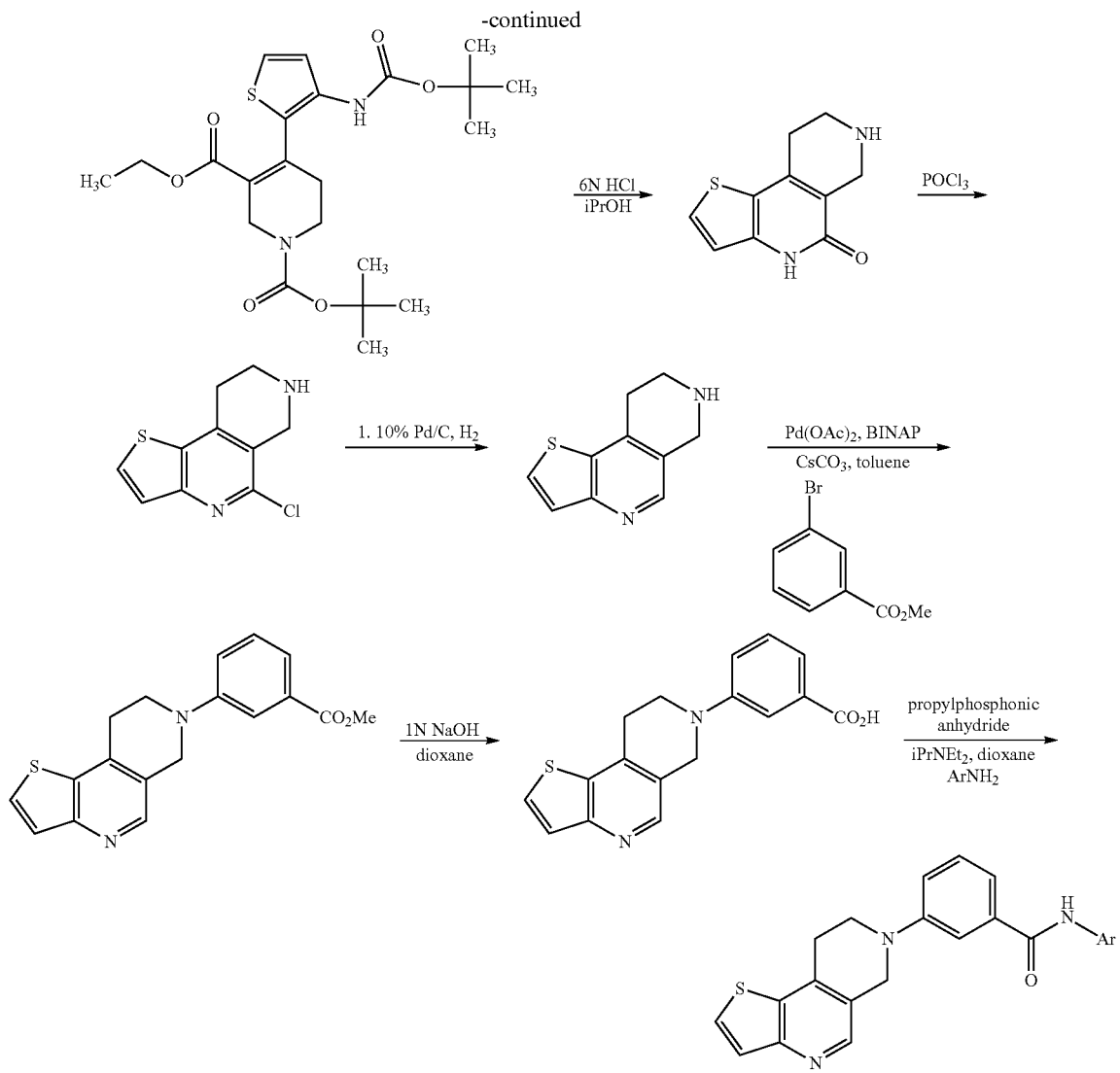

At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I.

The present invention is not to be limited in scope by the exemplified embodiments which are intended as illustrations of single aspects of the invention only. Indeed, various modifications of the invention in addition to those described herein will become apparent to those skilled in the art from the foregoing description.

DETAILED DESCRIPTION OF THE INVENTION

The present invention relates to a method of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders, which comprises administering a pharmaceutical composition comprising a therapeutically effective amount of at least one kinase inhibitor as described herein.

In another aspect, the invention provides the use of at least one kinase inhibitor for the manufacture of a medicament for the treatment of a disease or a condition mediated by tyrosine kinases in a mammal.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds is performed according to the following methods; NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by medium pressure liquid chromatography, unless noted otherwise.

EXPERIMENTAL CONDITIONS

Preparation 1

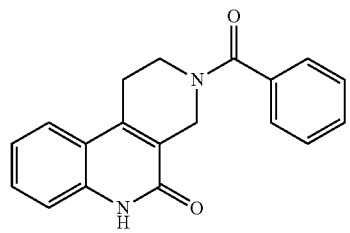 [SMILES: O=C(c1ccccc1)N1CCc2c(c(=O)[nH]c3ccccc23)C1]

3-benzoyl-2,3,4,6-tetrahydrobenzo[c]-2,7-naphthyridin-5(1H)-one

A 500 mL single-necked, round-bottomed flask was equipped with a heating/cooling bath, magnetic stirrer and stir bar, Dean-Stark trap, condenser, and nitrogen inlet. A solution containing N-benzoyl-4-piperidone (40.1 g, 197 mmol), pyrrolidine (37.9 g, 533 mmol), and toluene (200 mL) was refluxed for 4.5 hours under nitrogen. About 6 mL of water had collected in the trap. The volatiles were removed under reduced pressure, chasing sequentially with ethanol (45 mL) and toluene (45 mL), giving a reddish-brown residue. This residue was transferred into a 1 L single-necked, round-bottomed flask with dichloromethane (180 mL), the flask was fitted with a thermocouple and rubber septum, and a solution of phenyl isocyanate (23.97 g, 201 mmol) in dichloromethane (35 mL) was added drop-wise via syringe, keeping the temperature below 32° C. Once the addition was complete, the batch was stirred at ambient temperature for 16 hours. Volatiles were again removed under vacuum to provide a residue (~89 g). This material was taken-up in methanol (165 mL) and 12 N hydrochloric acid (50 mL). The resulting mixture was stirred for 4.5 hours, diluted with water (750 mL), and extracted into chloroform (1×200 mL; 2×150 mL). The combined organic layers were dried over anhydrous sodium sulfate (50 g), filtered, and concentrated to an orange semisolid (~73 g). Concentrated sulfuric acid (95 mL) was carefully added to the residue over 25 minutes, affording a brown syrup, which was heated to 100° C. for 30 minutes. The hot batch was transferred to a 2 L thick-walled conical flask, using 1,4-dioxane (65 mL) to complete the transfer. A large magnetic stir bar was introduced, followed by water (1000 mL), which was added drop-wise over 2 hours with vigorous stirring. The flask wall was scraped as needed to facilitate mixing. In this fashion, an amber solid was obtained. The solid was collected on a filter, rinsed with water (3×80 mL), and re-slurried in water (210 mL) and 37% ammonium hydroxide (6 mL) for 40 minutes. The solid was collected on a filter (slow) and dried in a vacuum oven at 50° C. to constant weight. The title compound was obtained as an amber solid (45.1 g, 75.2% yield) of 94.4% purity by HPLC analysis.

Preparation 2

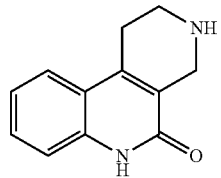 [SMILES: O=c1[nH]c2ccccc2c2c1CNCC2]

2,3,4,6-Tetrahydrobenzo[c]-2,7-naphthyridin-5(1H)-one

A 5 L, three-necked round-bottomed flask equipped with a heating bath, overhead stirrer, nitrogen inlet, condenser, and thermocouple was charged with 3-benzoyl-2,3,4,6-tetrahydrobenzo[c]-2,7-naphthyridin-5(1H)-one (84.2 g, 276.6 mmol) and aqueous 9 N hydrochloric acid (840 mL). The amber slurry was vigorously stirred while heating to 100-105° C. for 22 hours. The batch was cooled to 70° C., and ice-water (1000 mL) was added via a 500 mL addition funnel over 15 minutes with stirring. Next, 25 wt % sodium hydroxide (1000 mL) was added drop-wise to the stirred reaction via the addition funnel. Finally, aqueous 3 N sodium hydroxide (~500 mL) was added through the addition funnel. At this point, the pH of the batch measured >10. The mixture was diluted with water (1000 mL) and extracted with 18% (v/v) methanol in chloroform (12×2 L). The combined organic extracts were concentrated under vacuum to give a wet solid (~86 g). This material was swished in a mixture of tetrahydrofuran (110 mL), isopropanol (10 mL) and t-butyl methyl ether (25 mL) for 40 minutes. The solid was collected on a filter, rinsed with tetrahydrofuran (3×25 mL), and dried in a vacuum oven at 50° C. to constant weight to give the title compound (69% yield) with 98.8 A % purity by HPLC analysis.

Preparation 3

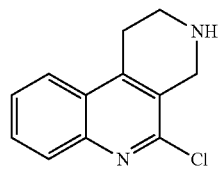 [SMILES: Clc1nc2ccccc2c2c1CNCC2]

5-chloro-1,2,3,4-tetrahydrobenzo[c]-2,7-naphthyridine

A slurry of 2,3,4,6-tetrahydrobenzo[c]-2,7-naphthyridin-5 (1H)-one (43.1 g, 215 mmol) in POCl₃ (260 mL) was vigorously stirred at reflux under nitrogen in a 2 L three-necked, round-bottomed flask equipped with a heating/cooling bath, mechanical stirrer, condenser, thermocouple, and nitrogen inlet. An aqueous base scrubber set-up was used to capture acidic exhaust gas. After 5 hours, the batch was homogeneous (indicating formation of the intermediate). Heating was continued for an additional 1 hour; then the mixture was allowed to slowly cool to ambient temperature and was stirred for 16 hours. When the starting material had been consumed, a 1 L addition funnel was fitted to the reaction flask, and the batch was cooled (ice-water) and carefully quenched by drop-wise addition of chilled water (~1 L). The quench addition was completed in ~6 hours. The resulting dark solution was stirred at ambient temperature for 18 hours. The batch was transferred to a 22 L round-bottomed flask equipped with a mechanical stirrer; the transfer was completed with water (13 L) to forestall salt precipitation that otherwise interferes with extraction. The pH was adjusted to 8.5-9 with aqueous 2 N sodium hydroxide (~3.9 L). Product was extracted with 17% (v/v) tetrahydrofuran in 2-methyltetrahydrofuran (4×2 L). All organic layers were combined and washed with saturated aqueous sodium chloride (2×150 mL) and dried over anhydrous sodium sulfate (300 g). After removal of the drying agent, solvent was removed under reduced pressure at 35-40° C. The crude solid was swished with 10% (v/v) t-butyl methyl ether in diethyl ether (220 mL) for 1 hour (to remove BHT) and collected on a filter using the filtrate to complete the transfer. The filter cake was rinsed with 10% (v/v) t-butyl methyl ether in diethyl ether (40 mL) and diethyl ether (30 mL), and dried in a vacuum oven to constant weight. In this fashion the title compound was obtained as a light yellow solid of (41.6 g, 87% yield) of 96 A % purity by HPLC assay.

Preparation 4

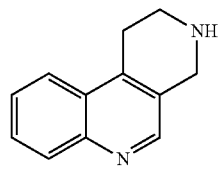 [SMILES: c1ccc2c3c(cnc2c1)CNCC3]

1,2,3,4-tetrahydrobenzo[c]-2,7-naphthyridine

A 2 L heavy-walled glass Parr vessel equipped with a magnetic stirrer and stir bar was charged under nitrogen with 5-chloro-1,2,3,4-tetrahydrobenzo[c]-2,7-naphthyridine (30.0 g, 137 mmol), 2:1 (v/v) isopropanol-tetrahydrofuran (1100 mL), triethylamine (40.0 g, 395 mmol) and 10% by weight palladium on carbon (3.0 g). The vessel was vacuum-degassed three times, releasing the vacuum with nitrogen each time, and evacuated three times, pressurizing with hydrogen each time. The hydrogen pressure was adjusted to 55 psi and the batch was stirred at ambient temperature for 16 hours. The catalyst was filtered-off through Celite (40 g) and the filter cake was rinsed with methanol (350 mL). The filtrate and rinse were concentrated to give a light yellow solid. The solid was swished with 5:1 (v/v) dichloromethane-methanol (50 mL), collected on a filter and dried to constant weight in a vacuum oven at 40° C. This first crop material was blended with additional product obtained from the filtrate after it was in turn purified by chromatography. The filtrate was concentrated in vacuo to provide a solid, which was dissolved in a little methanol and loaded onto a 10 g KP-Sil samplet. The samplet was allowed to dry before inserting it into a 100 g KP-Sil SNAP cartridge that had been pre-equilibrated with 3 CV of 10% (v/v) 5 N ammoniacal methanol-dichloromethane. The cartridge was attached to a Biotage unit and eluted with a gradient of 5 N ammoniacal methanol-dichloromethane as follows: 10% v/v (2 CV), 10-14% v/v (5 CV), 14-16% v/v (4 CV), and 16-18% v/v (4 CV). Pure fractions were pooled and concentrated under reduced pressure to obtain the product, which was thoroughly blended with the first crop material to afford the title compound as a yellow solid (21.5 g, 85% yield).

Example 1

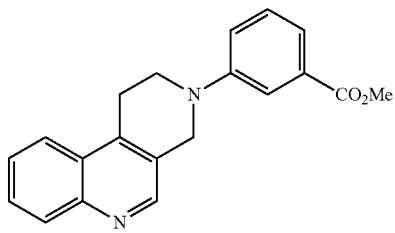 [SMILES: COC(=O)c1cccc(N2CCc3c(cnc4ccccc34)C2)c1]

Methyl 3-(1,4-dihydrobenzo[c]-2,7-naphthyridin-3 (2H)-yl)benzoate

A 1 L heavy-walled glass vessel equipped with a heating bath, magnetic stirrer, and a magnetic stir bar was charged with 1,2,3,4-tetrahydrobenzo[c]-2,7-naphthyridine (5.2 g, 28.3 mmol), methyl 3-bromo-benzoate (14.3 g, 66.5 mmol), palladium(II) acetate (886 mg, 4.0 mmol), X-phos (1.88 g, 3.95 mmol), and cesium carbonate (9.9 g, 30.4 mmol). A 1:1 solution of toluene and t-butanol (250 mL) was added, the vessel was sealed, and the contents were degassed three times by applying vacuum, each time releasing the vacuum with nitrogen.

The sealed vessel was heated at 120° C. for 21 hours. An aliquot assayed at this time by LC-MS showed most starting material to be unreacted. Additional catalyst solution was prepared from palladium(II) acetate (162 mg, 0.72 mmol) and X-phos (360 mg, 0.76 mmol) in degassed 3:2 toluene and t-butanol (50 mL) by stirring for 15 minutes to give deep purple solution. This solution was added to the reaction vessel, and stirring at 120° C. was continued for 22 hours. An second aliquot was assayed, which again indicated that much of the starting material remained. Another charge of catalyst solution was prepared as above from palladium(II) acetate (162 mg, 0.72 mmol) and X-phos (360 mg, 0.76 mmol) in degassed 3:2 toluene and t-butanol (50 mL). It was added to the reaction vessel and stirring at 120° C. was continued for 24 hours. After cooling, the batch was filtered through a pad of Celite (20 g) and the pad was rinsed with ethyl acetate (100 mL). The filtrate was concentrated under reduced pressure to a gummy residue (~21 g). This material was dissolved in dichloromethane (25 mL) and loaded onto a 34 g KP-Sil samplet, using additional dichloromethane (3×5 mL) to complete the transfer. The samplet was allowed to dry before inserting it into a 340 g KP-Sil SNAP cartridge pre-equilibrated with 3 CV of 20% (v/v) ethyl acetate-hexane. The cartridge was attached to a Biotage unit and eluted with a gradient of ethyl acetate-hexane as follows: 20-50% v/v (4 CV), 50-55% v/v (6 CV), 55% v/v (3 CV), and 55-60% v/v (2 CV). Pure fractions were combined and concentrated under reduced pressure to afford the title compound as a yellow foam (3.1 g, 34.5% yield) of 95 A % purity by HPLC assay.

Example 2

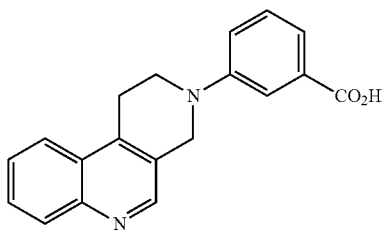 [SMILES: O=C(O)c1cccc(N2CCc3c(cnc4ccccc34)C2)c1]

3-(1,4-dihydrobenzo[c]-2,7-naphthyridin-3(2H)-yl) benzoic acid

A 250 mL single-necked, round-bottomed flask was equipped with a magnetic stirrer and stir bar, 125 mL addition funnel, and a nitrogen inlet. To the flask was added a solution of methyl 3-(1,4-dihydrobenzo[c]-2,7-naphthyridin-3(2H)-yl)benzoate (6.0 g, 18.84 mmol) in methanol (60 mL). The stirred batch was treated drop-wise over 10 minutes with a solution of 3 N aqueous sodium hydroxide (38 mL) and methanol (30 mL). A yellow precipitate appeared and re-dissolved. The batch was stirred at ambient temperature for 18 hours. Solvent was removed under reduced pressure and the stirred aqueous residue was acidified to pH 6-7 with 3 N aqueous hydrochloric acid (~38 mL). The resulting slurry was stirred at 23° C. for 2 hours. The solid was collected on a filter and rinsed with water (4 mL). More product was extracted from the filtrate with a 2:1 (v/v) mixture of 2-methyltetrahydro-furan-tetrahydrofuran (30×300 mL). The combined organic extracts were concentrated in vacuo to provide a residue. This residue was transferred to a small fritted glass funnel where it was swished consecutively with water (5 mL), 4:1 (v/v) tetrahydrofuran-methanol (20 mL), 8:1 (v/v) dichloromethane-methanol (8 mL), and 5:1 (v/v) dichloro-methane-methanol (9 mL), sucking the solvent through the frit each time. This material was then thoroughly mixed with the first crop and placed in a small fritted glass funnel. An final swish with diethyl ether (25 mL) was performed and the solid was dried at 23° C. in a vacuum oven to constant weight. In this way the title compound was obtained as a bright yellow solid (4.7 g, 83% yield) of >99 A % purity by HPLC analysis.

Example 3

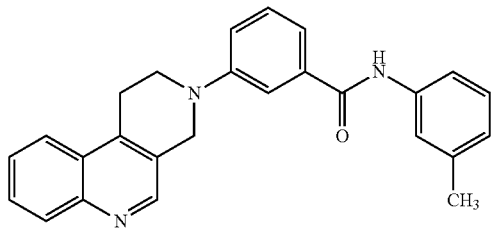 [SMILES: Cc1cccc(NC(=O)c2cccc(N3CCc4c(cnc5ccccc45)C3)c2)c1]

3-(1,4-dihydrobenzo[c]-2,7-naphthyridin-3(2H)-yl)-N-(3-methylphenyl)benzamide

To a mixture of 3-(1,4-dihydrobenzo[c]-2,7-naphthyridin-3(2H)-yl)benzoic acid (0.20 mmol, 61 mg) and triethylamine (0.40 mmol, 0.056 mL) in 1.6 mL DMF at rt was added propylphosphonic anhydride solution (50 wt % in EtOAc, 0.24 mmol, 0.143 mL). After 15 min at rt, meta-toluidine (0.30 mmol, 0.032 mL) was added and the reaction stirred at rt for 18 hours. The reaction was quenched into dilute aqueous $Na_2CO_3$ solution, extracted into EtOAc, the EtOAc layer washed with $H_2O$, dilute aqueous $Na_2CO_3$ solution, brine, dried with anhydrous $Na_2SO_4$ and concentrated. The resulting solid was chromatographed eluting with $CHCl_3$/EtOAc and then recrystallized from EtOAc/hexane to give the title compound as an off-white solid (38 mg, 48%).

$^1$H NMR (DSMO-d6) δ: 10.10 (br. s, 1H), 8.81 (s, 1H), 8.07 (dd, J=8.2, 0.9 Hz, 1H), 8.02 (dd, J=8.2, 0.9 Hz, 1H), 7.70-7.77 (m, 1H), 7.56-7.68 (m, 4H), 7.31-7.44 (m, 3H), 7.24 (t, J=7.8 Hz, 1H), 6.93 (d, J=7.3 Hz, 1H), 4.66 (s, 2H), 3.80 (t, J=5.7 Hz, 2H), 3.32-3.37 (m, 2H), 2.32 (s, 3H).

Example 4

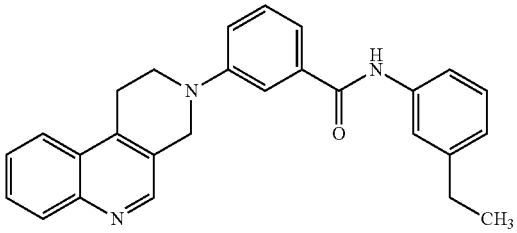 [SMILES: CCc1cccc(NC(=O)c2cccc(N3CCc4c(cnc5ccccc45)C3)c2)c1]

3-(1,4-dihydrobenzo[c]-2,7-naphthyridin-3(2H)-yl)-N-(3-ethylphenyl)benzamide

In a manner similar to Example 3, 3-(1,4-dihydrobenzo[c]-2,7-naphthyridin-3(2H)-yl)benzoic acid (0.20 mmol, 61 mg) and 3-ethylaniline (0.30 mmol, 0.037 mL) were reacted to give the title compound as an off-white solid (43 mg, 53%).

$^1$H NMR (DSMO-d6) δ: 10.11 (br. s, 1H), 8.81 (s, 1H), 8.07 (dd, J=8.4, 1.0 Hz, 1H), 8.02 (dd, J=8.2, 0.9 Hz, 1H), 7.70-7.77 (m, 1H), 7.59-7.68 (m, 4H), 7.31-7.44 (m, 3H), 7.26 (t, J=7.8 Hz, 1H), 6.96 (d, J=7.6 Hz, 1H), 4.67 (s, 2H), 3.80 (t, J=5.7 Hz, 2H), 3.32-3.36 (m, 2H), 2.61 (q, J=7.6 Hz, 2H), 1.21 (t, J=7.6 Hz, 3H).

Example 5

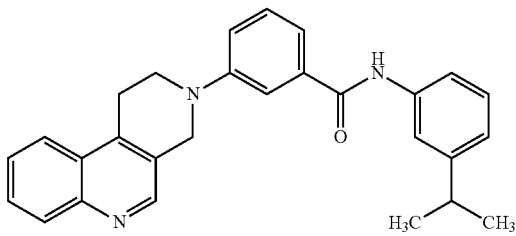 [SMILES: CC(C)c1cccc(NC(=O)c2cccc(N3CCc4c(cnc5ccccc45)C3)c2)c1]

3-(1,4-dihydrobenzo[c]-2,7-naphthyridin-3(2H)-yl)-N-(3-isopropylphenyl)benzamide To a mixture of 3-(1,4-dihydrobenzo[c]-2,7-naphthyridin-3(2H)-yl)benzoic acid (0.10 mmol, 30 mg) and triethylamine (0.20 mmol, 0.028 mL) in 1.0 mL DMF at rt was added propylphosphonic anhydride solution (50 wt % in EtOAc, 0.12 mmol, 0.072 mL). After 15 min at rt, 3-isopropylaniline (0.15 mmol, 0.021 mL) was added and the reaction stirred at rt for 4 hours. The reaction was quenched into dilute aqueous $Na_2CO_3$ solution, extracted into EtOAc, the EtOAc layer washed with $H_2O$, dilute aqueous $Na_2CO_3$ solution, brine, dried with anhydrous $Na_2SO_4$ and rotary evaporated. The resulting solid was triturated with EtOAc/hexane to give the title compound as a light beige solid (22 mg, 52%).

$^1$H NMR (DSMO-d6) δ: 10.12 (br. s, 1H), 8.81 (s, 1H), 8.07 (dd, J=8.4, 1.0 Hz, 1H), 8.02 (dd, J=8.4, 1.0 Hz, 1H), 7.70-7.77 (m, 1H), 7.60-7.68 (m, 4H), 7.31-7.45 (m, 3H), 7.27 (t, J=7.9 Hz, 1H), 6.99 (d, J=7.6 Hz, 1H), 4.67 (s, 2H), 3.80 (t, J=5.9 Hz, 2H), 3.33-3.37 (m, 2H), 2.88 (spt, J=6.9 Hz, 1H), 1.23 (d, J=6.7 Hz, 6H).

Example 6

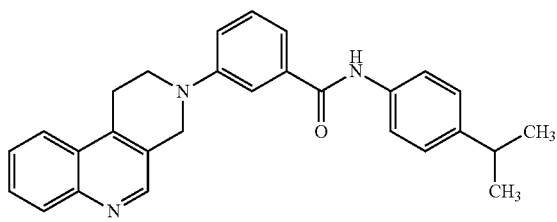 [SMILES: CC(C)c1ccc(NC(=O)c2cccc(N3CCc4c(cnc5ccccc45)C3)c2)cc1]

3-(1,4-dihydrobenzo[c]-2,7-naphthyridin-3(2H)-yl)-N-(4-isopropylphenyl)benzamide To a mixture of 3-(1,4-dihydrobenzo[c]-2,7-naphthyridin-3(2H)-yl)benzoic acid (0.20 mmol, 61 mg) and triethylamine (0.40 mmol, 0.056 mL) in 2.0 mL 1,2-dichloroethane at rt was added propylphosphonic anhydride solution (50 wt % in EtOAc, 0.24 mmol, 0.143 mL). After 10 min at rt, 4-isopropylaniline (0.30 mmol, 0.043 mL) was added and the reaction stirred at rt for 1 hour. Then an additional 0.015 mL 4-isopropylaniline was added, the reaction heated at 60° C. for 5 min, then continued at rt for 3 hours. The reaction was quenched into dilute aqueous $Na_2CO_3$ solution, extracted into EtOAc, the EtOAc layer washed with $H_2O$, dilute aqueous $Na_2CO_3$ solution, brine, dried with anhydrous $Na_2SO_4$ and rotary evaporated. The resulting solid was recrystallized from EtOAc/hexane to give the title compound as an off-white solid (52 mg, 62%).

$^1$H NMR (DSMO-d6) δ: 10.11 (br. s, 1H), 8.81 (s, 1H), 8.07 (dd, J=8.2, 0.9 Hz, 1H), 8.02 (dd, J=8.4, 1.0 Hz, 1H), 7.61-7.77 (m, 5H), 7.31-7.44 (m, 3H), 7.20-7.25 (m, 2H), 4.66 (s, 2H), 3.80 (t, J=5.7 Hz, 2H), 3.32-3.37 (m, 2H), 2.87 (spt, J=6.8 Hz, 1H), 1.21 (d, J=7.0 Hz, 6H).

Example 7

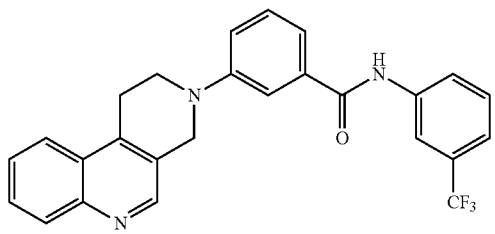 [SMILES: O=C(Nc1cccc(C(F)(F)F)c1)c1cccc(N2CCc3c(cnc4ccccc34)C2)c1]

3-(1,4-dihydrobenzo[c]-2,7-naphthyridin-3(2H)-yl)-N-[3-(trifluoromethyl)phenyl]benzamide To a mixture of 3-(1,4-dihydrobenzo[c]-2,7-naphthyridin-3(2H)-yl)benzoic acid (0.20 mmol, 61 mg), triethylamine (0.40 mmol, 0.056 mL), and catalytic DMAP in 2.0 mL 1,2-dichloroethane at rt was added propylphosphonic anhydride solution (50 wt % in EtOAc, 0.24 mmol, 0.143 mL). After 10 min at rt, 3-(trifluoromethyl)aniline (0.30 mmol, 0.037 mL) was added and the reaction stirred at rt for 24 hours. The reaction was quenched into dilute aqueous $Na_2CO_3$ solution, extracted into EtOAc, the EtOAc layer washed with $H_2O$, dilute aqueous $Na_2CO_3$ solution, brine, dried with anhydrous $Na_2SO_4$ and rotary evaporated. The resulting solid was recrystallized from EtOAc/hexane to give the title compound as a light yellow solid (59 mg, 66%).

$^1$H NMR (Acetone-d6) δ: 9.78 (br. s., 1H), 8.82 (s, 1H), 8.33 (s, 1H), 8.02-8.12 (m, 3H), 7.75-7.78 (m, 1H), 7.69-7.75 (m, 1H), 7.57-7.66 (m, 2H), 7.36-7.48 (m, 4H), 4.70 (s, 2H), 3.87 (t, J=5.9 Hz, 2H), 3.41 (t, J=5.9 Hz, 2H).

Preparation 5

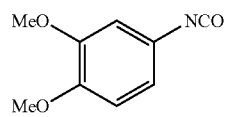

3,4-dimethoxyphenyl isocyanate

A 3 L, three-necked, round-bottomed flask was equipped with a heating/cooling bath, magnetic stirrer and stir bar, condenser, 500 mL addition funnel, thermocouple, nitrogen inlet, heating bath, vacuum distillation apparatus. To a stirred solution of 3,4-dimethoxyaniline (81.9 g, 535 mmol) in xylenes (1400 mL) was added via the addition funnel, a 4 N solution of hydrogen chloride in 1,4-dioxane (295 mL, 1180 mmol) at ambient temperature. This mixture was stirred at ~25° C. for 30 minutes, before it was heated to reflux under a slow $N_2$ stream. Neat triphosgene (200.0 g, 674 mmol) was added to the refluxing stirred mixture in portions via the addition funnel over 45 minutes. Upon completion of the addition, the batch was refluxed for another hour. After cooling to ~60° C., the batch was concentrated under reduced pressure to remove most of the solvent. The oily residue was distilled under high vacuum (b.p. 84-88° C. @ 0.92 mmHg) to afford the title compound as an oil (93.0 g, 97%).

Preparation 6

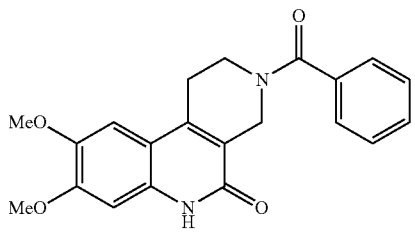 [SMILES: COc1cc2[nH]c(=O)c3c(c2cc1OC)CCN(C(=O)c1ccccc1)C3]

3-benzoyl-8,9-dimethoxy-2,3,4,6-tetrahydrobenzo[c]-2,7-naphthyridin-5(1H)-one

A 500 mL, three-necked, round-bottomed flask was equipped with a heating/cooling bath, magnetic stirrer and stir bar, Dean-Stark trap, condenser and nitrogen inlet. A solution of N-benzoyl-4-piperidone (16.24 g, 80 mmol) and pyrrolidine (15.0 g, 17.6 mL, 211 mmol) in toluene (250 mL) was refluxed for 4.5 hours using a Dean-Stark trap under nitrogen. After that period of time, ~2.5 mL of water had collected in the trap. An aliquot of the cooled reaction mixture was taken, concentrated in vacuo, and assayed by $^1$H NMR to determine completeness. Volatiles were removed under reduced pressure; the residue was dissolved in ethanol (45 mL), which was removed under reduced pressure, followed by dissolution in toluene (45 mL) and concentration in vacuo to a reddish-brown residue.

This material was dissolved with dichloromethane (160 mL) and a solution of 3,4-dimethoxyphenyl isocyanate (14.3 g, 80 mmol) in dichloromethane (40 mL) was added drop-wise with stirring, keeping the temperature below 28° C. The batch was stirred at ambient temperature for 16 hours. Solvent was removed under reduced pressure to give an amber foam.

The residue was dissolved in methanol (200 mL) and treated with aqueous 12 N hydrochloric acid (40 mL). The batch was stirred at 23° C. for 4.5 hours; after diluting with water (80 mL), it was extracted with dichloromethane (3×140 mL). The combined organic layers were dried over sodium sulfate anhydrous (50 g), filtered, and concentrated in vacuo to an orange semi-solid (25.6 g).

This material was mechanically stirred in a cooling bath and cautiously treated drop-wise over about 30 minutes with 98% by weight sulfuric acid (300 mL), keeping the internal temperature at <25° C. Assay of the resulting syrupy brown batch by LCMS indicated that the reaction was done. The mixture was carefully poured into vigorously stirred ice-water (2400 mL), and the stirred mixture was allowed to cool to and was held at ambient temperature for several hours. The resulting solid was collected in a fritted glass funnel (slow filtration), washed well with water, and dried to constant weight in a vacuum oven at 50° C. Thus was obtained the title compound as an amber solid (20.0 g, 69%) of 95% purity by HPLC assay.

Preparation 7

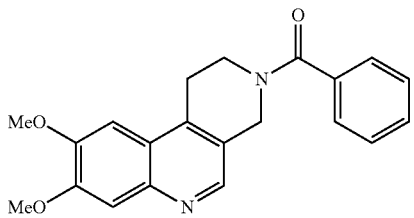 [SMILES: COc1cc2ncc3c(c2cc1OC)CCN(C(=O)c1ccccc1)C3]

3-benzoyl-8,9-dimethoxy-1,2,3,4-tetrahydrobenzo[c]-2,7-naphthyridine

A 2 L, three-necked, round-bottomed flask was equipped with a heating/cooling bath, magnetic stirrer and stir bar, 60 mL addition funnel, thermocouple, thermocouple adapter with a nitrogen inlet. The flask was charged with triethylamine (43 mL, 31.2 g, 308 mmol), 3-benzoyl-8,9-dimethoxy-2,3,4,6-tetrahydrobenzo[c]-2,7-naphthyridin-5 (1H)-one (30.2 g, 83 mmol), and dichloromethane (850 mL). The resulting slurry was stirred for 15 minutes at 22° C. and cooled to −18° C. Neat trifluoromethanesulfonic anhydride (34 mL, 202 mmol) was added drop-wise via an addition funnel over 40 minutes, keeping the temperature at −12 to −18° C. Upon completion of the addition, the mixture was warmed to 0° C. over 40 minutes and stirred at 0° C. for 2 hours. Solvents were stripped under reduced pressure. A solution of dichloro[1,1'-bis(diphenylphos-phino)ferrocene]palladium(II) dichloromethane adduct (4.72 g, 5.78 mmol) in a solution of degassed N,N-dimethylformamide (520 mL) and Et$_3$N (120 mL, 87.1 g, 861 mmol) was added to the residue and the batch was degassed by bubbling N$_2$ through it for 10 minutes. Degassed formic acid (15.8 mL, 419 mmol) was added over 1 minute via syringe and the stirred solution was heated to 55° C. Additional dichloro[1,1'-bis(diphenylphosphino) ferrocene]palladium(II) dichloromethane adduct (3.20 g, 3.92 mmol) was added after 20 minutes and the batch was heated at 55° C. for another 1 hour. At that time, assay by HPLC showed the reaction to be complete. Concentration in vacuo afforded 149 g of crude dark brown oil, which was dissolved in dichloromethane (180 mL) and loaded into a Biotage® unit (340 g KP-Sil cartridge equilibrated with dichloromethane). The column was eluted isocratically with dichloromethane (8 CV). The product containing fractions were combined and concentrated under reduced pressure; the resulting oil (105 g) was swished with ethyl acetate (520 mL) to give the title compound as a grey solid (13.0 g, 45% yield).

Preparation 8

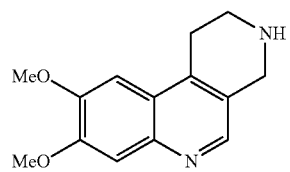

8,9-dimethoxy-1,2,3,4-tetrahydrobenzo[c]-2,7-naphthyridine

A 2 L three-necked, round-bottomed flask, was equipped with a magnetic stirrer and stir bar, condenser, heating bath, thermocouple and nitrogen inlet. A stirred solution of 3-benzoyl-8,9-dimethoxy-1,2,3,4-tetrahydrobenzo[c]-2,7-naphthyridine (25.9 g, 74.4 mmol) and LiOH.H$_2$O (34.4 g, 819 mmol) in methanol (800 mL) and water (55 mL) was heated at gentle reflux (internal temperature 62-66° C.) for 20 hours. Solvents were removed under reduced pressure and the residue was stirred in a mixture of methanol (180 mL) and dichloromethane (3 L) overnight. The batch was washed with saturated aqueous sodium chloride (0.5 L) diluted with water (0.4 L), and the separated organic layer was dried over anhydrous sodium sulfate (100 g). Removal of the drying agent by filtration and evaporation of solvent in vacuo gave a crude dark brown solid (12.1 g). The crude product was stirred in refluxing isopropanol (35 mL) for 1 hour, cooled to 22° C., and collected on a fritted glass funnel to afford the title compound as a grey solid (10.6 g, 58% yield).

Example 8

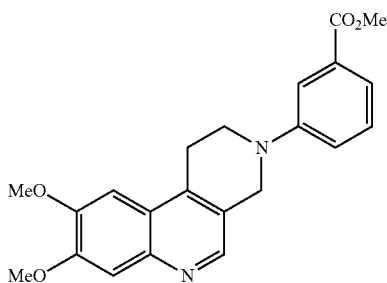 [SMILES: COC(=O)c1cccc(N2CCc3c(cnc4cc(OC)c(OC)cc34)C2)c1]

8,9-dimethoxy-1,2,3,4-tetrahydrobenzo[c]-2,7-naphthyridine

A 1 L heavy-walled pressure bottle was equipped with a threaded Teflon stopper with a quick disconnect gas inlet, magnetic stirrer and stir bar, heating bath and thermocouple. The pressure bottle was charged with 8,9-dimethoxy-1,2,3,4-tetrahydrobenzo[c]-2,7-naphthyridine (4.39 g, 18.0 mmol), methyl 3-iodobenzoate (7.08 g, 27.0 mmol), 2-(dicyclohexylphosphino)-2',4',6'-tri-i-propyl-1,1'-biphenyl (1.72 g, 36.0 mmol), palladium(II) acetate (0.404 g, 18.0 mmol), cesium carbonate (8.80 g, 27.0 mmol) and a degassed 5:1 mixture of toluene and t-butanol (270 mL). The fully charged vessel was vacuum-degassed with nitrogen a few times, sealed under nitrogen (5 psi), and the contents stirred at 100° C. for 18 hours. Assay by LCMS indicated that reaction was complete at that time. After cooling, the batch was filtered through Celite (25 g), and the filter cake washed with dichloromethane (75 mL). The filtrate and rinse were concentrated in vacuo to a residue. This crude product was dissolved in dichloromethane (5 mL) and loaded onto a 10 g KP-Sil samplet. After drying, the samplet was loaded into a Biotage® unit (100 g KP-Sil cartridge equilibrated with 3 CV dichloromethane) and eluted with a linear gradient of 1-4% by volume methanol in dichloromethane, 28 CV). Pure fractions were combined and concentrated under reduced pressure to afford the title compound as a yellow solid (6.0 g, 88% yield).

Example 9

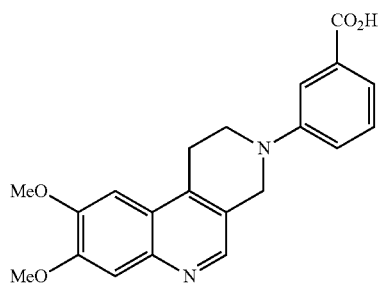 [SMILES: COc1cc2ncc3c(c2cc1OC)CCN(c1cccc(C(=O)O)c1)C3]

3-(8,9-dimethoxy-1,4-dihydrobenzo[c]-2,7-naphthyridin-3(2H)-yl)benzoic acid hydrochloride A 250 mL, single-necked, round-bottomed flask was equipped with a magnetic stirrer and stir bar and a nitrogen inlet. A mixture of 8,9-dimethoxy-1,2,3,4-tetrahydrobenzo[c]-2,7-naphthyridine (4.40 g, 116 mmol), aqueous 1.5 N potassium hydroxide (46.6 mL, 69.9 mmol), of tetrahydrofuran (100 mL), and methanol (25 mL) was stirred under nitrogen at 22° C. for 18 hours. An aliquot taken at that time and assayed by LCMS showed no starting material. The batch was acidified with aqueous 12 N hydrochloric acid (8.5 mL), added drop-wise, and the mixture was stirred at 22° C. for one hour. The solids were collected on a fritted glass funnel and rinsed with tetrahydrofuran (5 mL) and water (5 mL). The filter cake was dried to constant weight under reduced pressure at 22° C. to afford the title compound as a yellow solid (4.25 g, 83% yield).

Example 10

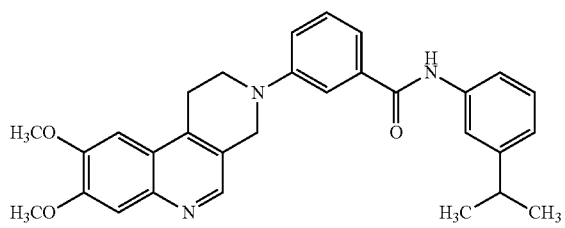 [SMILES: COc1cc2ncc3c(c2cc1OC)CCN(c1cccc(C(=O)Nc2cccc(C(C)C)c2)c1)C3]

3-(8,9-dimethoxy-1,4-dihydrobenzo[c]-2,7-naphthyridin-3(2H)-yl)-N-(3-isopropylphenyl)benzamide To a mixture of 3-(8,9-dimethoxy-1,4-dihydrobenzo[c]-2,7-naphthyridin-3(2H)-yl)benzoic acid hydrochloride (0.25 mmol, 100 mg) and N, N-diisopropylethylamine (0.75 mmol, 0.131 mL) in 2.0 mL DMF at rt was added propylphosphonic anhydride solution (50 wt % in EtOAc, 0.325 mmol, 0.193 mL). After 5 min at rt, 3-isopropylaniline (0.375 mmol, 0.053 mL) and catalytic DMAP was added and the reactions continued for 2 hours. Then an additional 0.050 mL propylphosphonic anhydride solution and 0.025 mL 3-isopropylaniline was added and the reaction continued for 19 hours. The reaction was quenched into dilute aqueous Na$_2$CO$_3$ solution, extracted into EtOAc, the EtOAc layer washed with H$_2$O, brine, dried with anhydrous Na$_2$SO$_4$ and rotary evaporated.

The resulting oil was chromatographed eluting with CHCl₃/EtOAc and then recrystallized from EtOAc/hexane to give the title compound as a white solid (20 mg, 17%).

¹H NMR (CDCl₃) δ: 8.54 (s, 1H), 7.92 (s, 1H), 7.64-7.66 (m, 1H), 7.57 (t, J=1.8 Hz, 1H), 7.46-7.50 (m, 1H), 7.44 (s, 1H), 7.36-7.42 (m, 1H), 7.30 (t, J=7.9 Hz, 1H), 7.17-7.27 (m, 2H), 7.09 (s, 1H), 7.01-7.06 (m, 1H), 4.58 (s, 2H), 4.04 (s, 3H), 4.02 (s, 3H), 3.79 (t, J=5.9 Hz, 2H), 3.27 (t, J=5.9 Hz, 2H), 2.93 (spt, J=6.9 Hz, 1H), 1.28 (d, J=7.0 Hz, 6H).

Example 11

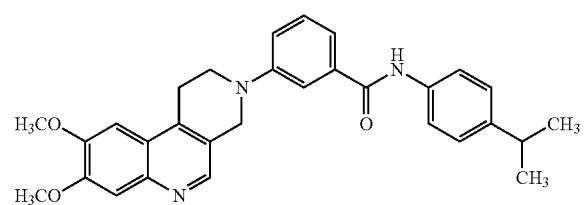 [SMILES: COc1cc2ncc3c(c2cc1OC)CCN(c1cccc(C(=O)Nc2ccc(C(C)C)cc2)c1)C3]

3-(8,9-dimethoxy-1,4-dihydrobenzo[c]-2,7-naphthyridin-3(2H)-yl)-N-(4-isopropylphenyl)benzamide To a mixture of 3-(8,9-dimethoxy-1,4-dihydrobenzo[c]-2,7-naphthyridin-3(2H)-yl)benzoic acid hydrochloride (0.38 mmol, 152 mg), N, N-diisopropylethylamine (1.14 mmol, 0.199 mL), and catalytic DMAP in 2.0 mL DMF at rt was added propylphosphonic anhydride solution (50 wt % in EtOAc, 0.494 mmol, 0.293 mL). After 8 min at rt, 4-isopropylaniline (0.57 mmol, 0.081 mL) was added and the reactions continued for 1.8 hours. Then an additional 0.050 mL propylphosphonic anhydride solution and 0.020 mL 4-isopropylaniline was added, the mixture briefly heated to 80° C. 3 times, and then continued at rt for 2 hours. The reaction was quenched into dilute aqueous Na₂CO₃ solution, extracted into EtOAc, the EtOAc layer washed with H₂O, brine, dried with anhydrous Na₂SO₄ and rotary evaporated. The resulting solid was chromatographed eluting with CHCl₃/EtOAc/MeOH and then triturated with EtOAc to give the title compound as a light yellow solid (23 mg, 13%).

¹H NMR (CDCl₃) δ: 8.55 (s, 1H), 7.85 (s, 1H), 7.63-7.65 (m, 1H), 7.55-7.60 (m, 2H), 7.44 (s, 1H), 7.36-7.42 (m, 1H), 7.17-7.27 (m, 4H), 7.10 (s, 1H), 4.59 (s, 2H), 4.04 (s, 3H), 4.03 (s, 3H), 3.79 (t, J=5.9 Hz, 2H), 3.27 (t, J=5.9 Hz, 2H), 2.91 (spt, J=7.0 Hz, 1H), 1.26 (d, J=7.0 Hz, 6H)

Preparation 9

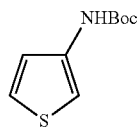 [SMILES: CC(C)(C)OC(=O)Nc1ccsc1]

tert-Butyl-N-(thiophen-3-yl)carbamate

According to the method described in WO2005040110, a mixture of 3-aminothiophene oxalate (15 g, 79.29 mmol) in water (150 ml) was basified with ammonium hydroxide and extracted with dichloromethane (3×70 ml). The combined organic extracts were dried (MgSO₄), filtered and concentrated to a brown oil (6.35 g). A solution of the free base and triethylamine (8.93 ml, 64.04 mmol) in dichloromethane (70 ml) was added dropwise to a cooled (0° C.) solution of Boc-anhydride (16.77 g, 76.85 mmol) in dichloromethane (35 ml) with stirring over a period of ~90 minutes. The reaction mixture was allowed to warm up to room temperature and stirred for 20 hours before quenching with water. After thorough mixing, the separated organic layer was dried (MgSO₄), filtered, and concentrated. Trituration with hexanes gave a beige, amorphous solid which was collected, washed with hexanes, and dried to give the title compound (6.31 g). Concentration of the hexane washings and elution of the residue through a flash column (silica gel 60, 230-400 mesh, 9:1 hexanes:EtOAc) gave an additional batch of the title compound (1.85 g, 64% total yield).

Preparation 10

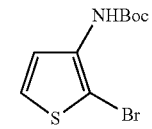

tert-Butyl-N-(2-bromothiophen-3-yl)carbamate

According to the method described in WO2005070916, A boiling solution of tert-Butyl-N-(thiophen-3-yl)carbamate (5.32 g, 26.70 mmol) in dichloromethane (260 ml) was treated portionwise with N-bromo-succinimide (4.73 g, 26.70 mmol) under vigorous stirring. After addition was complete, the heating bath temperature was raised to 65° C. and maintained for 20 minutes before allowing the reaction to cool to room temperature. The reaction mixture was washed with water, dried (MgSO₄), filtered, and concentrated. Elution through a flash column (silica gel 60, 230-400 mesh, 4:1 hexanes:EtOAc) gave a clear oil which crystallized on standing (7.24 g, 97%).

Preparation 11

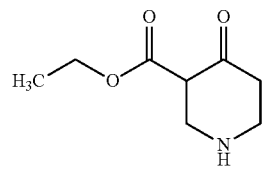

Ethyl 4-oxopiperidine-3-carboxylate

To a solution of ethyl 1-benzyl-4-oxopiperidine-3-carboxylate (360.0 g, 1.21 mol) in EtOH (6.7 L) was added wet Pd/C (55.0 g) under N₂ that then was replaced by H₂. The reaction mixture was stirred at rt for 4 h, filtered and concentrated to give a crude product. The crude product was slurried with EtOH (200 mL) for 2 h and then filtered. The filtered cake was washed with MTBE and the combined organic phases were concentrated to give the title compound (222.0 g, 1.07 mol, 88.4%).

Preparation 12

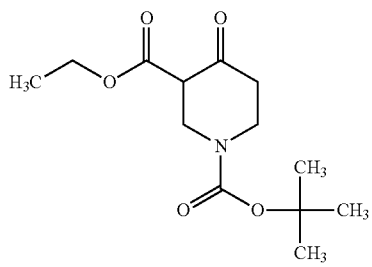 [SMILES: CCOC(=O)C1CN(C(=O)OC(C)(C)C)CCC1=O]

1-tert-butyl 3-ethyl
4-oxopiperidine-1,3-dicarboxylate

To a solution of ethyl 4-oxopiperidine-3-carboxylate (180.0 g, 0.87 mol, 1.0 eq.) in DCM (2.7 L) was added Et₃N (352.14 g, 3.48 mol, 4.0 eq.) dropwise at 15° C. and stirred for 30 min followed by addition of (BOC)₂O (210.0 g, 0.96 mol, 1.10 eq.) maintaining the temperature below 10° C. The resulted mixture was stirred at rt overnight, and concentrated to give a crude product that was stirred with hexane (3.5 L) for 1 h and filtered. The filtered cake was washed with hexanes. The combined organic phase was concentrated to furnish the title compound (226.0 g, 0.83 mol, 95.4%).

Preparation 13

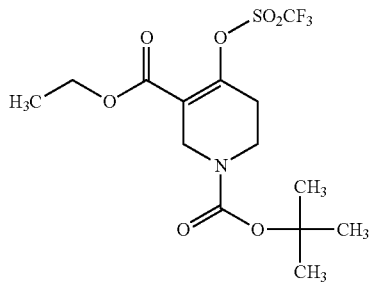

1-tert-butyl 3-ethyl 4-(((trifluoromethyl)sulfonyl)
oxy)-5,6-dihydropyridine-1,3(2H)-dicarboxylate To a solution of 1-tert-butyl 3-ethyl 4-oxopiperidine-1,3-dicarboxylate (120.0 g, 0.44 mol, 1.00 eq.) in toluene was added N,N-diisopropylethyl-amine (85.50 g, 0.66 mol, 1.51 eq.) at −40° C., and stirred for 30 min followed by addition of trifluoromethanesulfonic anhydride (137.0 g, 0.49 mol, 1.10 eq.). The resulted solution was stirred at −30° C. for 2 h, and then raised to rt and filtered. The filtered cake was washed with toluene and the combined organic phase was concentrated to give a crude product (223.0 g) that was used immediately for the next step.

Preparation 14

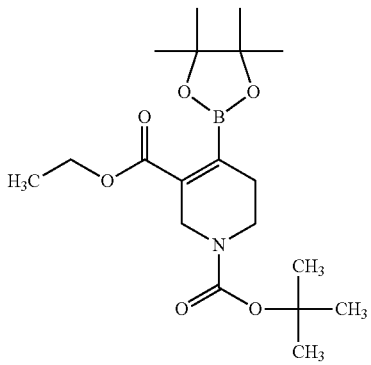 [SMILES: CCOC(=O)C1=C(B2OC(C)(C)C(C)(C)O2)CCN(C(=O)OC(C)(C)C)C1]

4-(4,4,5,5-Tetramethyl-[1,3,2]dioxaborolan-2-yl)-5,
6-dihydro-2H-pyridine-1,3-dicarboxylic acid 1-tert-
butyl ester 3-ethyl ester To a solution of 1-tert-butyl 3-ethyl 4-(((trifluoromethyl)sulfonyl)oxy)-5,6-dihydropyridine-1,3(2H)-dicarboxylate (crude 223 g from the Preparation 13) in dioxane (1.8 L) was added bis-pinacol diboron (112.7 g, 0.44 mol), Pd(dppf)Cl₂ (17 g, 23.23 mmol), and potassium acetate (130.40 g, 1.33 mol). The reaction mixture was stirred at 85-90° C. for 2 h, diluted with EtOAc (2 L) and H₂O (2 L). The organic phase was washed with H₂O (2×4 L), sat. NaCl (2 L), dried, and filtered. The filtered cake was washed with EtOAc, and the combined organic phase was concentrated at 35° C. to furnish a crude product (239 g) that was stirred with hexanes (1.5 L) for 1 h, and filtered. The filtered cake was washed with hexanes and the combined organic phase was concentrated and purified by chromatography (EtOAc/hexane) to give the title compound (85.56 g, 0.22 mol, 51.7% for two steps).

Preparation 15

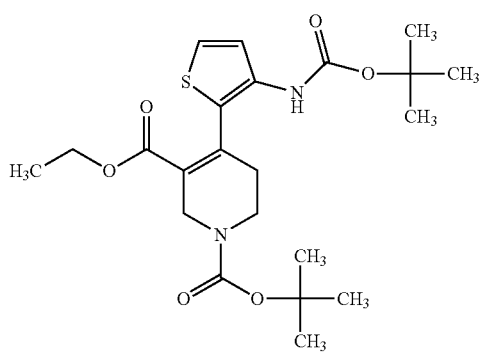 [SMILES: CCOC(=O)C1=C(c2sccc2NC(=O)OC(C)(C)C)CCN(C(=O)OC(C)(C)C)C1]

1-tert-Butyl-3-ethyl-4-(3-{[tert-butoxy)carbonyl]
amino}thiophen-2-yl)-1,2,5,6-tetrahydro-pyridine-1,
3-dicarboxylate A mixture of tert-butyl-N-(2-bromothiophen-3-yl)carbamate (6.29 g, 22.61 mmol), 4-(4,4,5,5-tetramethyl-[1,3,2]dioxaborolan-2-yl)-5,6-dihydro-2H-pyridine-1,3-dicarboxylic acid 1-tert-butyl ester 3-ethyl ester (17.24 g, 45.22 mmol), palladium(II)acetate (508 mg, 2.261 mmol), S-Phos (1.86 g, 4.522 mmol) and potassium carbonate (6.25 g, 45.22 mmol) in 8:1 (v/v) 1,4-dioxane:water (330 ml) was heated at 80° C. for 3 hours and allowed to cool to room temperature. The insolubles were filtered off (celite) and the filtrate was concentrated. Elution through a flash column (silica gel 60, 230-400 mesh, 4:1 hexanes:EtOAc to 1:1 hexanes:EtOAc) gave the title compound as a viscous, orange oil which crystallized on standing (5.11 g, 50%).

Preparation 16

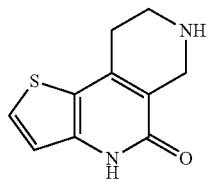 [SMILES: O=c1[nH]c2ccsc2c2c1CNCC2]

3a,6,7,8,9,9b-hexahydrothieno[3,2-c]-2,7-naphthyridin-5(4H)-one

A solution of 1-tert-butyl-3-ethyl-4-(3-{[(tert-butoxy)carbonyl]amino}thiophen-2-yl)-1,2,5,6-tetrahydro-pyridine-1,3-dicarboxylate (1.44 g, 3.17 mmol) in acetone (70 ml) was treated with 5-6 N HCl solution in i-PrOH (10 ml) and the reaction mixture was stirred at room temperature for 2-6 hours. The solvent was removed in vacuo and the residue was taken up in water (~70 ml), neutralized with saturated aqueous sodium bicarbonate, and treated with a small volume of EtOAc. After stirring for approx. 30 minutes, the off-white, amorphous precipitate was collected, washed with water, ethyl acetate, and dried to give the title compound (382 mg, 58%).

Preparation 17

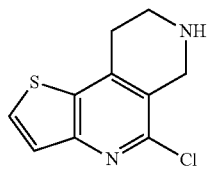 [SMILES: Clc1nc2ccsc2c2c1CNCC2]

5-Chloro-6,7,8,9-tetrahydrothieno[3,2-c]-2,7-naphthyridine

A mixture of 3a,6,7,8,9,9b-hexahydrothieno[3,2-c]-2,7-naphthyridin-5(4H)-one (2.69 g, 13.04 mmol) in phosphorus oxychloride (70 ml) was heated at 80-85° C. with stirring for 24 hours and allowed to cool to room temperature. The excess solvent was removed in vacuo and the residue was carefully quenched with ice water. The aqueous mixture was treated with solid NaOH until product precipitation ceased (pH ~5) and the off-white, amorphous solid was collected, washed with water, and dried to give the title compound (2.51 g, 86%).

Preparation 18

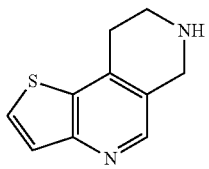 [SMILES: c1cc2ncc3c(c2s1)CCNC3]

6,7,8,9-Tetrahydrothieno[3,2-c]-2,7-naphthyridine

A mixture of 5-Chloro-6,7,8,9-tetrahydrothieno[3,2-c]-2,7-naphthyridine (3.22 g, 14.33 mmol), 10% Pd on C (500 mg) and ammonium formate (8.13 g, 128.97 mmol) in EtOH (125 ml) was heated at 80° C. for 24 hours. Analytical data (TLC, MS) confirmed complete removal of chlorine to give both the title compound along with the N-formyl analog. Upon cooling, the catalyst was filtered off (celite) and the filtrate was treated with $NaOH_{(aq.)}$ until pH ~14. The alkaline reaction mixture was refluxed for 33 hours, cooled, filtered and concentrated. Elution through a flash column (silica gel 60, 230-400 mesh, 9:1 EtOAc:7M $NH_3$ in MeOH) gave the title compound as a viscous yellow oil which crystallized on standing (1.96 g, 72%).

Example 12

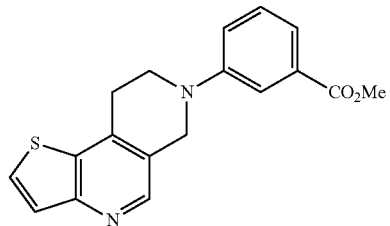 [SMILES: COC(=O)c1cccc(N2CCc3c(cnc4ccsc34)C2)c1]

Methyl 3-(8,9-dihydrothieno[3,2-c]-2,7-naphthyridin-7(6H)-yl)benzoate

A mixture of 6,7,8,9-Tetrahydrothieno[3,2-c]-2,7-naphthyridine (3.0 g, 15.77 mmol, prepared as previously described), methyl-3-bromobenzoate (3.90 g, 18.14 mmol), palladium(II)acetate (354 mg, 1.577 mmol), racemic BINAP (982 mg, 1.577 mmol) and cesium carbonate (7.19 g, 22.08 mmol) in toluene (270 ml) was heated at 100° C. with stirring for 18 hours. Upon cooling to room temperature, the insolubles were filtered off (celite) and washed with EtOAc. The washing was combined with the filtrate and concentrated. Elution through a flash column (silica gel 60, 230-400 mesh, EtOAc) gave the product as a yellow glass (3.54 g, 69%). MS (APCl): $(M+1)^+=325$;

$^1$H-NMR (DMSO-$d_6$, 6): 8.58 (s, 1H), 8.02 (d, 1H), 7.57 (s, 1H), 7.53 (d, 1H), 7.36 (s, 3H), 4.59 (s, 2H), 3.82 (s, 3H), 3.73 (t, 2H), 3.05 (t, 2H).

Example 13

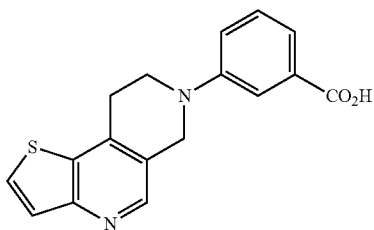 [SMILES: O=C(O)c1cccc(N2CCc3c(cnc4ccsc34)C2)c1]

3-(8,9-dihydrothieno[3,2-c]-2,7-naphthyridin-7(6H)-yl)benzoic acid

A solution of methyl 3-(8,9-dihydrothieno[3,2-c]-2,7-naphthyridin-7(6H)-yl)benzoate (3.54 g, 10.91 mmol) in 1,4-dioxane (150 ml) was treated with 1.0 N NaOH$_{(aq.)}$ (32.73 ml, 32.73 mmol) and the reaction mixture was stirred at 90° C. for 3.5 hours. The solvent was removed in vacuo and the residue was partitioned between water and diethyl ether. The organic phase was discarded and the aqueous phase was acidified to pH ~4-5 with 1.0 N HCl$_{(aq.)}$. The resulting precipitate was collected, washed with water, EtOAc, and dried in vacuo at 35° C. to afford the title compound as a yellow, amorphous solid (2.66 g, 79%). MS (APCl): (M+1)$^+$=311;

$^1$H-NMR (DMSO-d$_6$, δ): 8.58 (s, 1H), 8.04 (d, 1H), 7.58 (s, 1H), 7.53 (d, 1H), 7.34 (s, 3H), 4.58 (s, 2H), 3.72 (t, 2H), 3.05 (t, 2H).

Example 14

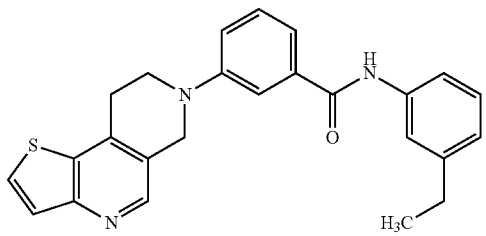 [SMILES: CCc1cccc(NC(=O)c2cccc(N3CCc4c(cnc5ccsc45)C3)c2)c1]

3-(8,9-dihydrothieno[3,2-c]-2,7-naphthyridin-7(6H)-yl)-N-(3-ethylphenyl)benzamide To a mixture of 3-(8,9-dihydrothieno[3,2-c]-2,7-naphthyridin-7(6H)-yl)benzoic acid (0.113 mmol, 35 mg), N, N-diisopropylethylamine (0.339 mmol, 0.059 mL), and catalytic DMAP in 1.2 mL 1,2-dichloroethane at rt was added propylphosphonic anhydride solution (50 wt % in EtOAc, 0.136 mmol, 0.081 mL). After 7 min at rt, 3-ethylaniline (0.17 mmol, 0.021 mL) was added and the reaction stirred at rt for 5 hours. The reaction was quenched into dilute aqueous NaHCO$_3$ solution, extracted with EtOAc, the EtOAc layer washed with H$_2$O, dilute aqueous NaHCO$_3$ solution, brine, dried with anhydrous Na$_2$SO$_4$ and rotary evaporated. The resulting oil was chromatographed eluting with EtOAc/CDCl$_3$ to give the title compound as a light yellow solid (32 mg, 69%).

$^1$H NMR (CDCl$_3$) δ: 8.52 (s, 1H), 7.89 (br. s., 1H), 7.67 (d, J=5.6 Hz, 1H), 7.62 (s, 1H), 7.53-7.58 (m, 2H), 7.46 (d, J=8.2 Hz, 1H), 7.35-7.42 (m, 1H), 7.22-7.32 (m, 2H), 7.15-7.21 (m, 1H), 7.00 (d, J=7.6 Hz, 1H), 4.60 (s, 2H), 3.77 (t, J=5.9 Hz, 2H), 3.15 (t, J=5.7 Hz, 2H), 2.67 (q, J=7.6 Hz, 2H), 1.26 (t, J=7.6 Hz, 3H).

VEGFR2 and PDGFRβ kinase potencies of select analogs was determined by the following assay:

VEGFR2 Kinase Assay:

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of 0-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N H$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of 0-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N H$_2$SO$_4$ to each well and read using a microplate ELISA reader set at 492 nm. IC$_{50}$ values for compound inhibition were calculated directly from graphs of optical density (arbitrary units) versus compound concentration following subtraction of blank values.

TABLE 2

In vitro VEGFR2 and PDGFRβ data

| Example Number | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 3 | 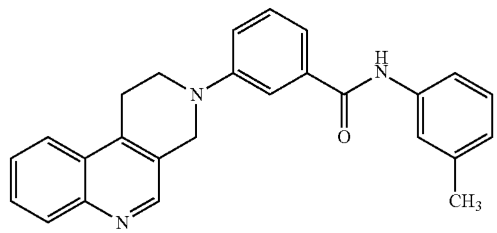 | 7 | 23 | 16 | na |
| 4 | 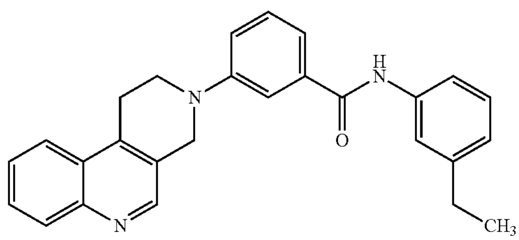 [SMILES: CCc1cccc(NC(=O)c2cccc(N3CCc4c(cnc5ccccc45)C3)c2)c1] | 6 | 19 | 10 | 58 |
| 5 | 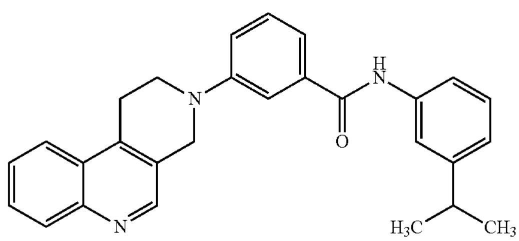 [SMILES: CC(C)c1cccc(NC(=O)c2cccc(N3CCc4c(cnc5ccccc45)C3)c2)c1] | 7 | 30 | 15 | 200 |
| 6 | 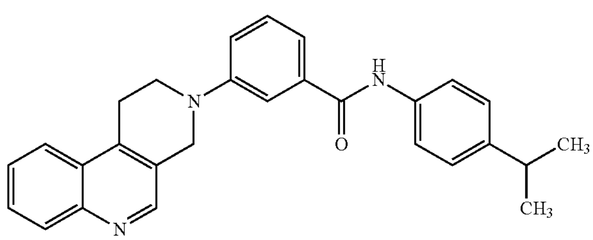 [SMILES: CC(C)c1ccc(NC(=O)c2cccc(N3CCc4c(cnc5ccccc45)C3)c2)cc1] | 8 | 71 | 16 | na |
| 7 | 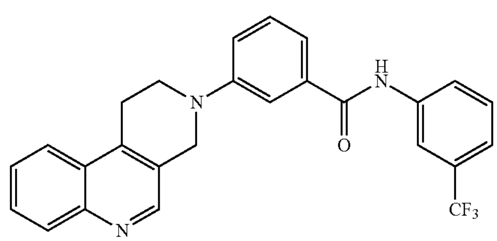 [SMILES: O=C(Nc1cccc(C(F)(F)F)c1)c1cccc(N2CCc3c(cnc4ccccc34)C2)c1] | 10 | 46 | 14 | 103 |
| 10 | 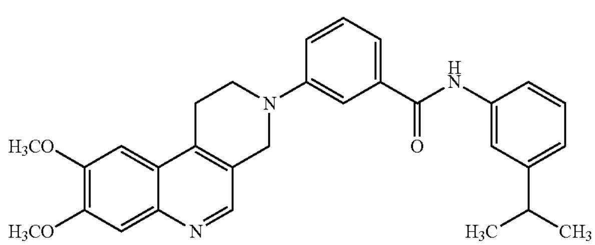 [SMILES: COc1cc2ncc3c(c2cc1OC)CCN(c1cccc(C(=O)Nc2cccc(C(C)C)c2)c1)C3] | 7 | na | 11 | na |

TABLE 2-continued

In vitro VEGFR2 and PDGFRβ data

| Example Number | Structure | VEGFR2 Enzyme Assay (IC$_{50}$ nM) | VEGFR2 Cellular Assay (IC$_{50}$ nM) | PDGFRβ Enzyme Assay (IC$_{50}$ nM) | PDGFRβ Cellular Assay (IC$_{50}$ nM) |
|---|---|---|---|---|---|
| 11 | 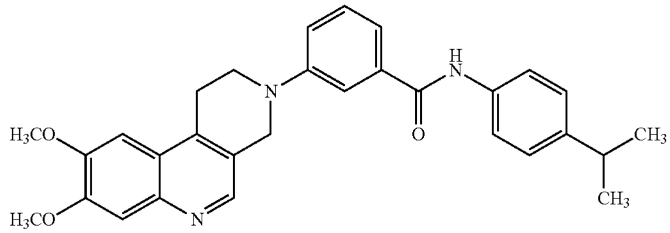 [SMILES: COc1cc2ncc3c(c2cc1OC)CCN(c1cccc(C(=O)Nc2ccc(C(C)C)cc2)c1)C3] | 9 | 20 | 18 | na |
| 14 | 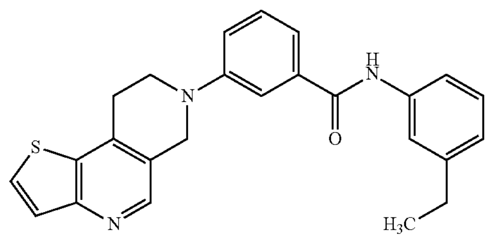 [SMILES: CCc1cccc(NC(=O)c2cccc(N3CCc4c(cnc5ccsc45)C3)c2)c1] | 5 | 12 | 7 | na |

We claim:

1. A compound represented by Formula I, its enantiomers, diastereoisomers, tautomers, or a pharmaceutically acceptable salt thereof:

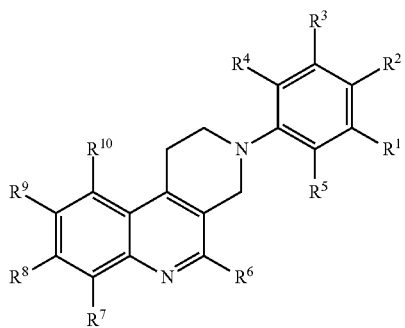

wherein:
$R^1$ is COOR$^{11}$ or CONR$^{12}$R$^{13}$;
$R^2$ is hydrogen;
$R^3$ is hydrogen;
$R^4$ is hydrogen;
$R^5$ is hydrogen;
$R^6$ is hydrogen;
$R^7$ is hydrogen;
$R^8$ is hydrogen or methoxy;
$R^9$ is hydrogen or methoxy;
$R^{10}$ is hydrogen;
$R^{11}$ is hydrogen or methyl;
$R^{12}$ is hydrogen;
$R^{13}$ is phenyl substituted with C$_{1-3}$ alkyl or trifluoromethyl.

2. A compound according to claim 1, wherein:
$R^1$ is COOR$^{11}$.

3. A compound according to claim 1, wherein:
$R^1$ is CONR$^{12}$R$^{13}$.

4. A compound according to claim 1, wherein:
$R^1$ is COOR$^{11}$; and
$R^{11}$ is hydrogen.

5. A compound according to claim 1, wherein:
$R^1$ is COOR$^{11}$; and
$R^{11}$ is methyl.

6. A compound according to claim 1, wherein:
$R^1$ is CONR$^{12}$R$^{13}$.

7. A compound according to claim 1, wherein:
$R^1$ is CONR$^{12}$R$^{13}$;
$R^{13}$ is phenyl substituted with C$_{1-3}$ alkyl or trifluoromethyl.

8. A compound according to claim 1, selected from:
3-(1,4-dihydrobenzo[c]-2,7-naphthyridin-3(2H)-yl)benzoic acid;
3-(1,4-dihydrobenzo[c]-2,7-naphthyridin-3(2H)-yl)-N-(3-methylphenyl)benzamide;
3-(1,4-dihydrobenzo[c]-2,7-naphthyridin-3(2H)-yl)-N-(3-ethylphenyl)benzamide;
3-(1,4-dihydrobenzo[c]-2,7-naphthyridin-3(2H)-yl)-N-(3-isopropylphenyl)benzamide;
3-(1,4-dihydrobenzo[c]-2,7-naphthyridin-3(2H)-yl)-N-(4-isopropylphenyl)benzamide;
3-(1,4-dihydrobenzo[c]-2,7-naphthyridin-3(2H)-yl)-N-[3-(trifluoromethyl)phenyl]benzamide;
8,9-dimethoxy-1,2,3,4-tetrahydrobenzo[c]-2,7-naphthyridine;
3-(8,9-dimethoxy-1,4-dihydrobenzo[c]-2,7-naphthyridin-3(2H)-yl)benzoic acid;
3-(8,9-dimethoxy-1,4-dihydrobenzo[c]-2,7-naphthyridin-3 (2H)-yl)-N-(3-isopropylphenyl)benzamide; and
3-(8,9-dimethoxy-1,4-dihydrobenzo[c]-2,7-naphthyridin-3 (2H)-yl)-N-(4-isopropylphenyl)benzamide.

9. A compound selected from:
Methyl 3-(1,4-dihydrobenzo[c]-2,7-naphthyridin-3(2H)-yl)benzoate;
methyl 3-(8,9-dihydrothieno[3,2-c]-2,7-naphthyridin-7(6H)-yl)benzoate;
3-(8,9-dihydrothieno[3,2-c]-2,7-naphthyridin-7(6H)-yl)benzoic acid; and 3-(8,9-dihydrothieno[3,2-c]-2,7-naphthyridin-7(6H)-yl)-N-(3-ethylphenyl)benzamide.

10. A pharmaceutical composition comprising as active ingredient a therapeutically effective amount of a compound according to claim 1 and a pharmaceutically acceptable adjuvant, diluent or carrier.

* * * * *